(12) United States Patent
Abdou

(10) Patent No.: US 8,876,874 B2
(45) Date of Patent: Nov. 4, 2014

(54) BONE SCREW SYSTEMS AND METHODS OF USE

(76) Inventor: M. Samy Abdou, San Diego, CA (US)

(*) Notice: Subject to any disclaimer, the term of this patent is extended or adjusted under 35 U.S.C. 154(b) by 1265 days.

(21) Appl. No.: 11/894,994

(22) Filed: Aug. 21, 2007

(65) Prior Publication Data
US 2008/0045963 A1 Feb. 21, 2008

Related U.S. Application Data

(60) Provisional application No. 60/839,014, filed on Aug. 21, 2006, provisional application No. 60/921,570, filed on Apr. 3, 2007.

(51) Int. Cl.
*A61B 17/70* (2006.01)
*A61B 17/86* (2006.01)

(52) U.S. Cl.
CPC ..... *A61B 17/7032* (2013.01); *A61B 2017/8655* (2013.01); *A61B 17/8685* (2013.01); *A61B 17/7038* (2013.01); *A61B 17/7037* (2013.01)
USPC .......................................... 606/305; 606/313

(58) Field of Classification Search
USPC ............ 606/60, 246–279, 300–320, 322–328
See application file for complete search history.

(56) References Cited

U.S. PATENT DOCUMENTS

| | | | |
|---|---|---|---|
| 824,983 A | 7/1906 | Farrington |
| 944,725 A | 12/1909 | Ferguson |
| 1,015,890 A | 1/1912 | Hyde |
| 1,213,599 A | 1/1917 | Dow |
| 1,785,709 A | 4/1930 | Campau |
| 2,248,054 A | 7/1941 | Becker |
| 2,329,398 A | 9/1943 | Duffy |
| 2,370,407 A | 2/1945 | McCartney |
| 2,574,352 A | 11/1951 | Senter |
| 3,037,596 A | 6/1962 | Fordyce |
| 3,072,423 A | 1/1963 | Charlton |
| 3,236,141 A | 2/1966 | Smith |
| 3,604,487 A | 9/1971 | Gilbert |
| 3,659,595 A | 5/1972 | Haboush |

(Continued)

FOREIGN PATENT DOCUMENTS

| | | |
|---|---|---|
| EP | 1180348 | 2/2002 |
| FR | 2781359 | 1/2000 |

(Continued)

OTHER PUBLICATIONS

Derwent English Abstract for French Patent Publication FR 2781359, published Jan. 28, 2000, entitled: "Osteosynthesis frame for spinal surgery has rod with clamps to hold cross bars with anchor screws". Accession No. 9867555.

(Continued)

*Primary Examiner* — Pedro Philogene
*Assistant Examiner* — Lynnsy Summitt
(74) *Attorney, Agent, or Firm* — Gazdzinski & Associates, PC

(57) ABSTRACT

The distal bone screw segment of a bone screw system is driven into bone. In a first state, the assembly permits relative motion between its component parts in order to facilitate the placement and correct alignment of an interconnecting rod that is used to couple multiple bone screw systems and/or other orthopedic devices. In a second state, the assembly provides relative immobilization between the assembly components and the inter-connecting rod.

36 Claims, 43 Drawing Sheets

(56) References Cited

U.S. PATENT DOCUMENTS

| | | | |
|---|---|---|---|
| 4,399,813 A | 8/1983 | Barber | |
| 4,699,076 A | 10/1987 | Curtis | |
| 4,711,232 A * | 12/1987 | Fischer et al. | 606/67 |
| 4,877,020 A | 10/1989 | Vich | |
| 4,903,692 A | 2/1990 | Reese | |
| 4,904,110 A | 2/1990 | Klein | |
| 4,969,886 A | 11/1990 | Cziffer et al. | |
| 5,052,711 A | 10/1991 | Pirkey et al. | |
| 5,252,016 A | 10/1993 | Schmid et al. | |
| 5,275,601 A | 1/1994 | Goglewski et al. | |
| 5,336,225 A | 8/1994 | Zang | |
| 5,352,231 A | 10/1994 | Brumfield et al. | |
| 5,354,292 A | 10/1994 | Braeuer et al. | |
| 5,360,429 A | 11/1994 | Jeanson et al. | |
| 5,366,455 A | 11/1994 | Dove et al. | |
| 5,423,826 A | 6/1995 | Coates et al. | |
| 5,437,672 A | 8/1995 | Alleyne | |
| 5,439,339 A | 8/1995 | Batchelor | |
| 5,474,555 A | 12/1995 | Puno | |
| 5,484,440 A | 1/1996 | Allard | |
| 5,531,747 A | 7/1996 | Ray | |
| 5,534,001 A | 7/1996 | Schlapfer et al. | |
| 5,534,027 A | 7/1996 | Hodorek | |
| 5,545,164 A | 8/1996 | Howland | |
| 5,558,674 A | 9/1996 | Heggeness et al. | |
| 5,569,250 A | 10/1996 | Sarver et al. | |
| 5,586,984 A | 12/1996 | Errico | |
| 5,591,166 A | 1/1997 | Bernhardt et al. | |
| 5,607,426 A | 3/1997 | Ralph et al. | |
| 5,616,142 A | 4/1997 | Yuan et al. | |
| 5,649,931 A | 7/1997 | Bryant et al. | |
| 5,669,912 A | 9/1997 | Spetzler | |
| 5,672,176 A * | 9/1997 | Biedermann et al. | 606/271 |
| 5,681,312 A | 10/1997 | Yuan et al. | |
| 5,735,853 A | 4/1998 | Olerud | |
| 5,876,402 A | 3/1999 | Errico et al. | |
| 5,964,762 A | 10/1999 | Biedermann et al. | |
| 5,971,987 A | 10/1999 | Huxel et al. | |
| 5,976,140 A | 11/1999 | Haas | |
| 5,993,449 A | 11/1999 | Schlapfer et al. | |
| 6,010,503 A | 1/2000 | Richelsoph et al. | |
| 6,033,170 A | 3/2000 | Gold | |
| 6,059,786 A | 5/2000 | Jackson | |
| 6,117,135 A | 9/2000 | Schlapfer et al. | |
| 6,139,549 A | 10/2000 | Keller | |
| 6,187,005 B1 | 2/2001 | Brace | |
| 6,251,112 B1 | 6/2001 | Jackson | |
| 6,254,602 B1 | 7/2001 | Justis | |
| 6,273,888 B1 | 8/2001 | Justis | |
| 6,290,703 B1 | 9/2001 | Ganem | |
| 6,306,136 B1 | 10/2001 | Baccelli | |
| 6,309,391 B1 | 10/2001 | Crandell et al. | |
| 6,331,179 B1 | 12/2001 | Freid et al. | |
| 6,355,038 B1 | 3/2002 | Pisharodi | |
| 6,355,040 B1 | 3/2002 | Richelsoph et al. | |
| 6,361,258 B1 | 3/2002 | Heesch | |
| RE37,665 E | 4/2002 | Ralph | |
| 6,368,320 B1 | 4/2002 | Le Couedic et al. | |
| 6,402,752 B2 | 6/2002 | Schaffler-Wachter et al. | |
| 6,471,705 B1 * | 10/2002 | Biedermann et al. | 606/271 |
| 6,547,790 B2 | 4/2003 | Harkey, III et al. | |
| 6,599,290 B2 | 7/2003 | Bailey et al. | |
| 6,645,207 B2 | 11/2003 | Dixon et al. | |
| 6,663,631 B2 | 12/2003 | Kuntz et al. | |
| 6,666,867 B2 | 12/2003 | Ralph et al. | |
| 6,679,883 B2 | 1/2004 | Hawkes et al. | |
| 6,723,100 B2 | 4/2004 | Biedermann et al. | |
| 6,827,722 B1 | 12/2004 | Schoenefeld | |
| 6,830,571 B2 | 12/2004 | Lenke et al. | |
| 6,855,147 B2 | 2/2005 | Harrington, Jr. | |
| 6,884,243 B2 | 4/2005 | Sellers | |
| 6,896,677 B1 * | 5/2005 | Lin | 606/266 |
| 6,979,334 B2 | 12/2005 | Dalton | |
| 7,232,441 B2 | 6/2007 | Altarac et al. | |
| 7,303,563 B2 | 12/2007 | Poyner et al. | |
| 7,503,918 B2 * | 3/2009 | Baccelli et al. | 606/269 |
| 7,621,942 B2 | 11/2009 | Piehl | |
| 7,625,396 B2 * | 12/2009 | Jackson | 606/305 |
| 7,691,129 B2 * | 4/2010 | Felix | 606/246 |
| 7,776,067 B2 * | 8/2010 | Jackson | 606/246 |
| 2002/0016595 A1 | 2/2002 | Michelson | |
| 2002/0049446 A1 | 4/2002 | Harkey, III et al. | |
| 2002/0055741 A1 | 5/2002 | Schlapfer et al. | |
| 2002/0099386 A1 | 7/2002 | Beger et al. | |
| 2002/0111628 A1 | 8/2002 | Ralph et al. | |
| 2002/0143328 A1 | 10/2002 | Shluzas et al. | |
| 2002/0169453 A1 | 11/2002 | Berger | |
| 2002/0183755 A1 | 12/2002 | Michelson et al. | |
| 2002/0188296 A1 | 12/2002 | Michelson | |
| 2003/0078583 A1 | 4/2003 | Biedermann et al. | |
| 2003/0125741 A1 | 7/2003 | Biedermann et al. | |
| 2003/0153913 A1 | 8/2003 | Altarac | |
| 2003/0167058 A1 | 9/2003 | Shluzas | |
| 2003/0199873 A1 | 10/2003 | Richelsoph et al. | |
| 2004/0133207 A1 | 7/2004 | Abdou | |
| 2004/0153070 A1 | 8/2004 | Barker et al. | |
| 2004/0204712 A1 | 10/2004 | Kolb et al. | |
| 2004/0204713 A1 | 10/2004 | Abdou | |
| 2004/0249380 A1 | 12/2004 | Glascott | |
| 2004/0267264 A1 * | 12/2004 | Konieczynski et al. | 606/73 |
| 2005/0010227 A1 | 1/2005 | Paul | |
| 2005/0033296 A1 | 2/2005 | Bono | |
| 2005/0033298 A1 | 2/2005 | Hawkes | |
| 2005/0096653 A1 * | 5/2005 | Doubler et al. | 606/61 |
| 2005/0119748 A1 * | 6/2005 | Reiley et al. | 623/17.11 |
| 2005/0154390 A1 | 7/2005 | Biedermann | |
| 2005/0177163 A1 | 8/2005 | Abdou | |
| 2005/0187555 A1 * | 8/2005 | Biedermann et al. | 606/72 |
| 2005/0228376 A1 | 10/2005 | Boomer et al. | |
| 2005/0273120 A1 | 12/2005 | Abdou | |
| 2005/0283153 A1 | 12/2005 | Poyner | |
| 2005/0288669 A1 | 12/2005 | Abdou et al. | |
| 2006/0015181 A1 | 1/2006 | Elberg | |
| 2006/0074488 A1 | 4/2006 | Abdou | |
| 2006/0085069 A1 | 4/2006 | Kim | |
| 2006/0088398 A1 | 4/2006 | Lund | |
| 2006/0089646 A1 | 4/2006 | Bonutti | |
| 2006/0149240 A1 * | 7/2006 | Jackson | 606/61 |
| 2006/0149278 A1 | 7/2006 | Abdou | |
| 2006/0155278 A1 | 7/2006 | Warnick | |
| 2006/0155284 A1 | 7/2006 | Doherty et al. | |
| 2006/0161152 A1 | 7/2006 | Ensign et al. | |
| 2006/0161154 A1 | 7/2006 | McAfee | |
| 2006/0173456 A1 * | 8/2006 | Hawkes et al. | 606/61 |
| 2006/0195089 A1 | 8/2006 | LeHuec et al. | |
| 2006/0217710 A1 | 9/2006 | Abdou | |
| 2006/0229610 A1 | 10/2006 | Piehl | |
| 2006/0229615 A1 | 10/2006 | Abdou | |
| 2006/0235387 A1 | 10/2006 | Peterman | |
| 2006/0241614 A1 | 10/2006 | Bruneau et al. | |
| 2007/0093817 A1 * | 4/2007 | Barrus et al. | 606/61 |
| 2007/0093829 A1 | 4/2007 | Abdou | |
| 2007/0106383 A1 | 5/2007 | Abdou | |
| 2007/0118121 A1 | 5/2007 | Purcell et al. | |
| 2007/0123867 A1 * | 5/2007 | Kirschman | 606/61 |
| 2007/0123869 A1 | 5/2007 | Chin et al. | |
| 2007/0123884 A1 | 5/2007 | Abdou | |
| 2007/0213732 A1 * | 9/2007 | Khanna et al. | 606/73 |
| 2007/0270813 A1 * | 11/2007 | Garamszegi | 606/61 |
| 2008/0015580 A1 * | 1/2008 | Chao | 606/61 |
| 2008/0015597 A1 * | 1/2008 | Whipple | 606/73 |
| 2008/0027430 A1 * | 1/2008 | Strauss et al. | 606/61 |
| 2008/0051783 A1 | 2/2008 | Null et al. | |
| 2008/0058810 A1 | 3/2008 | Abdou | |
| 2008/0147123 A1 | 6/2008 | Schermerhorn | |
| 2008/0154308 A1 * | 6/2008 | Sherman et al. | 606/265 |
| 2008/0161853 A1 * | 7/2008 | Arnold et al. | 606/246 |
| 2008/0243185 A1 * | 10/2008 | Felix et al. | 606/246 |
| 2008/0312655 A1 * | 12/2008 | Kirschman et al. | 606/60 |
| 2009/0030457 A1 * | 1/2009 | Janowski et al. | 606/246 |
| 2009/0163961 A1 * | 6/2009 | Kirschman | 606/301 |
| 2009/0210007 A1 * | 8/2009 | Levy et al. | 606/246 |
| 2009/0254125 A1 * | 10/2009 | Predick | 606/264 |
| 2010/0023061 A1 * | 1/2010 | Randol et al. | 606/278 |

(56) References Cited

U.S. PATENT DOCUMENTS

| | | |
|---|---|---|
| 2010/0076448 A1 | 3/2010 | Abdou |
| 2010/0121384 A1 | 5/2010 | Abdou |
| 2010/0152778 A1* | 6/2010 | Saint Martin ............... 606/279 |
| 2010/0241168 A1* | 9/2010 | Franck et al. ............... 606/250 |

FOREIGN PATENT DOCUMENTS

| FR | 2856271 | 12/2004 |
|---|---|---|
| WO | WO 2004/032726 | 4/2004 |
| WO | WO 2004/062482 | 7/2004 |
| WO | 2004/093702 | 11/2004 |
| WO | 2005/122922 | 12/2005 |
| WO | WO 2006/041963 | 4/2006 |
| WO | WO 2006045089 A2 * | 4/2006 |
| WO | WO 2006/058221 | 6/2006 |
| WO | WO 2006/089292 | 8/2006 |
| WO | 2006/096756 | 9/2006 |
| WO | WO 2007/041648 | 4/2007 |
| WO | WO 2007/044705 | 4/2007 |
| WO | WO 2007/044836 | 4/2007 |
| WO | WO 2007/056516 | 5/2007 |
| WO | WO 2007/059207 | 5/2007 |
| WO | WO 2008/024373 | 2/2008 |

OTHER PUBLICATIONS

Derwent English Abstract for French Patent Publication FR 2856271, published Dec. 24, 2004, Osteo-synthesis vertebral column plate, has connection head integrated with plate and movable in three directions of space so as to adapt itself to connection rod, and including opening to facilitate introduction of rod. Accession No. 4694557.

* cited by examiner

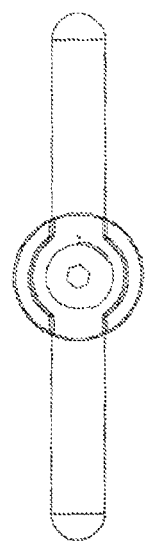
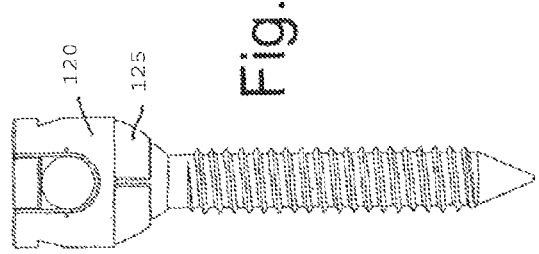
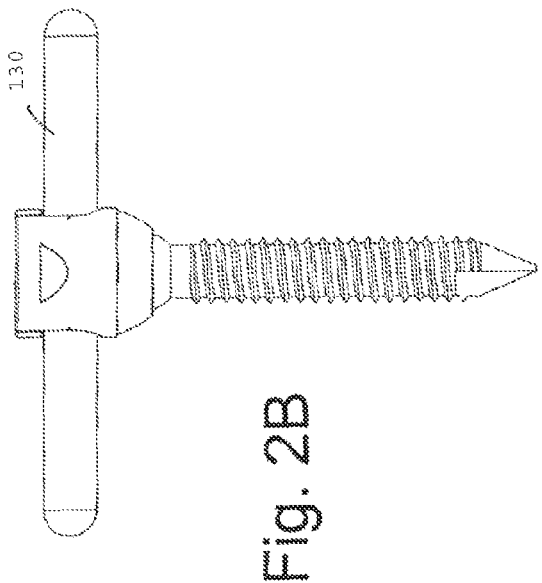

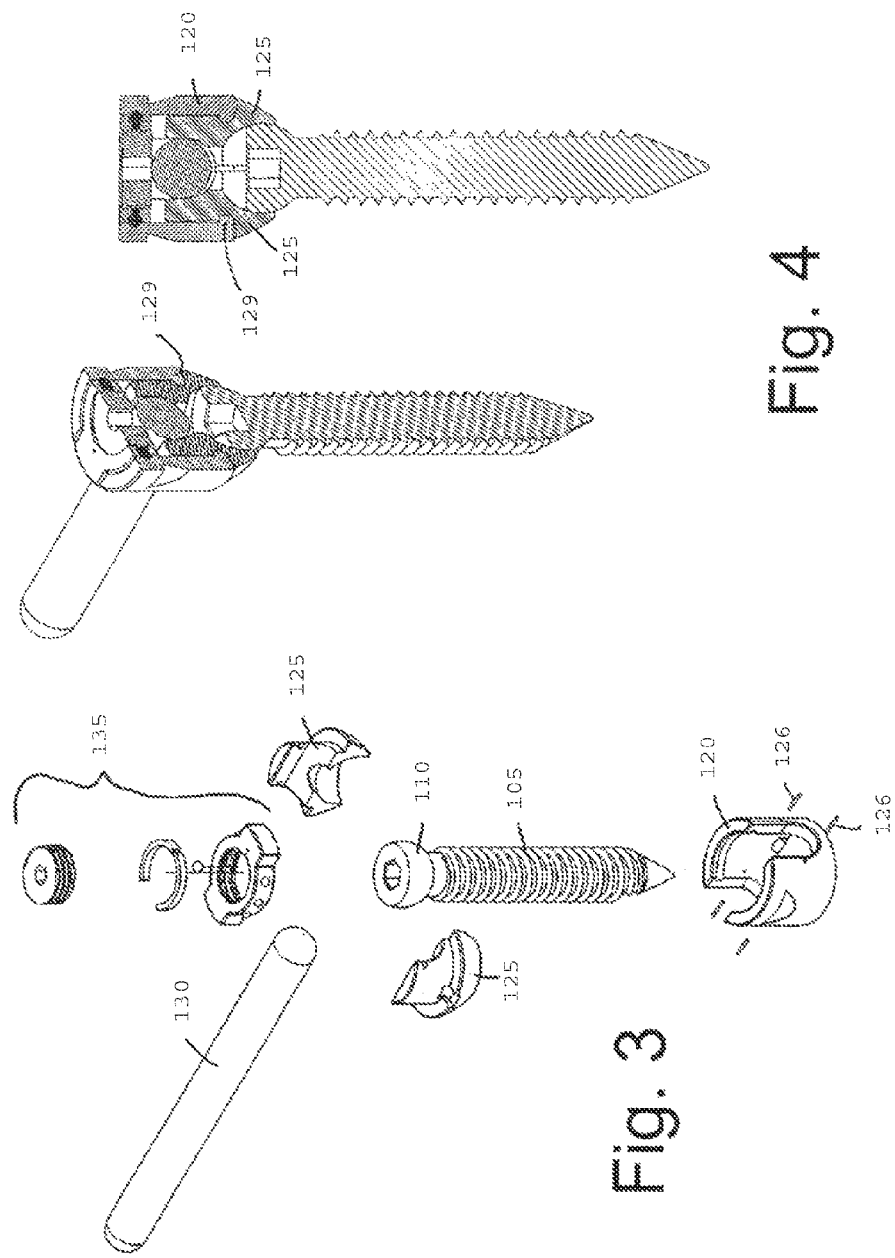

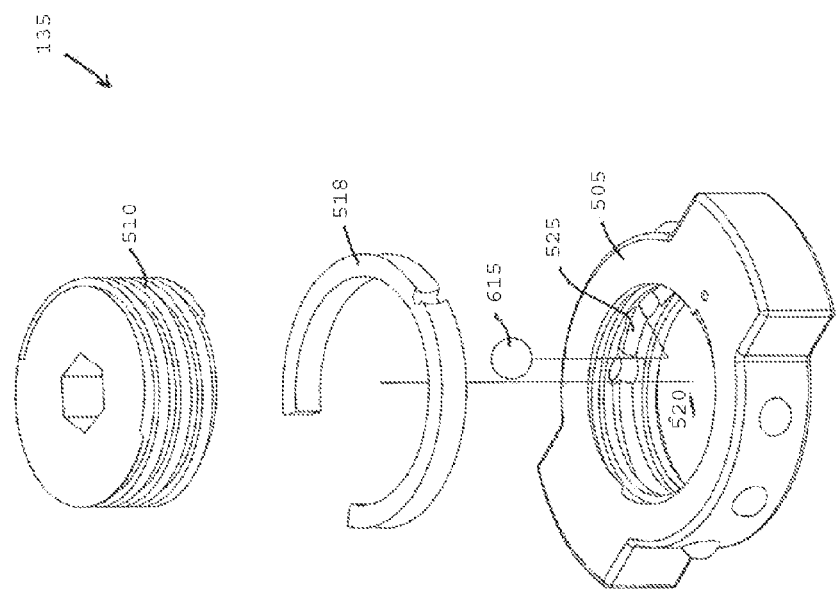

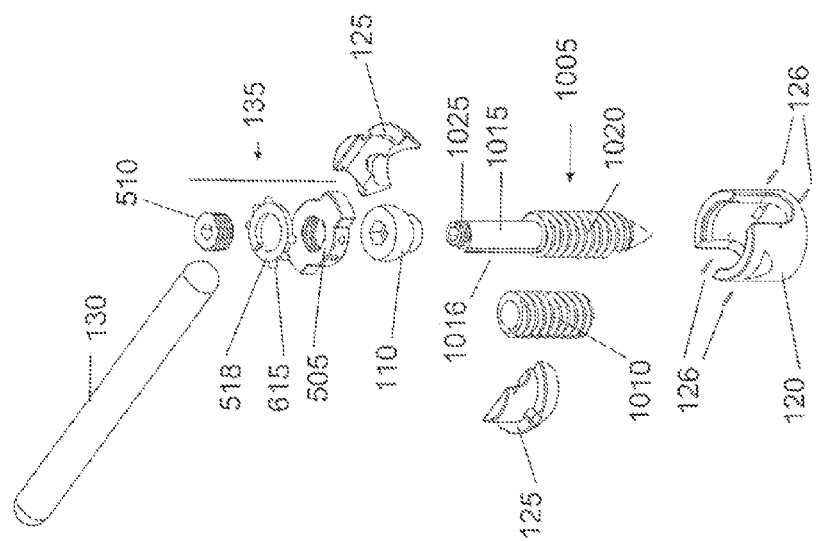

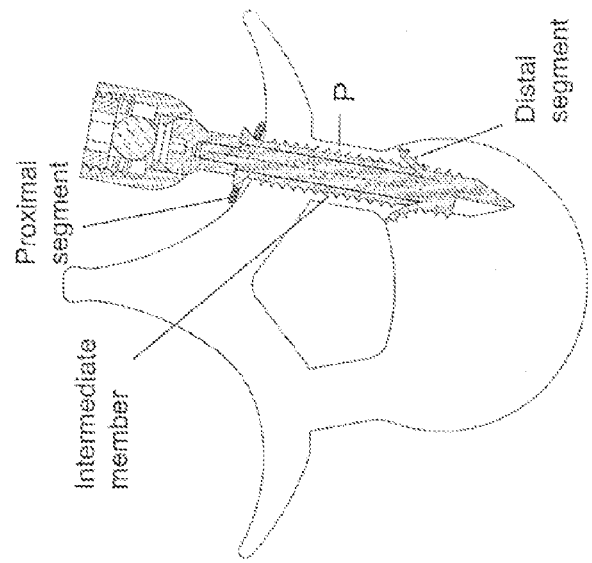
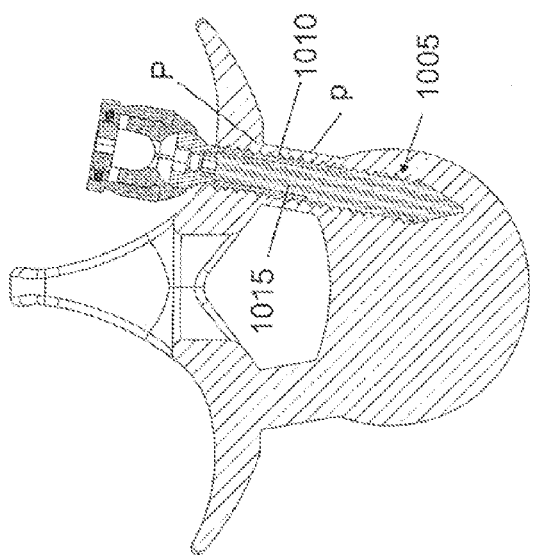
Fig. 11A
Fig. 11B

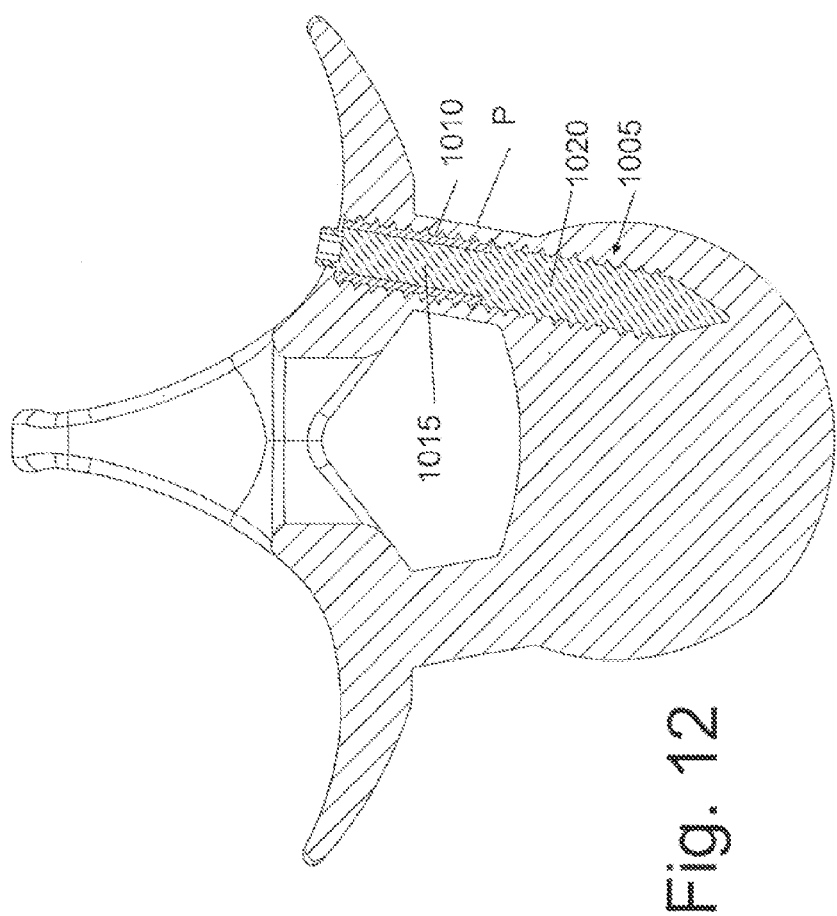

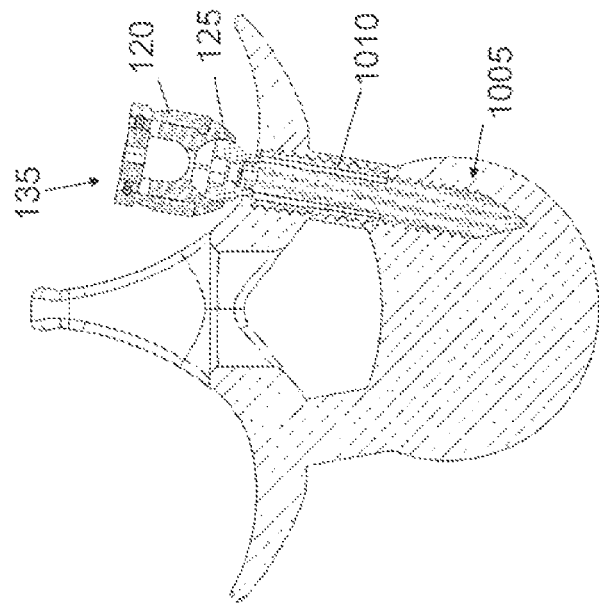
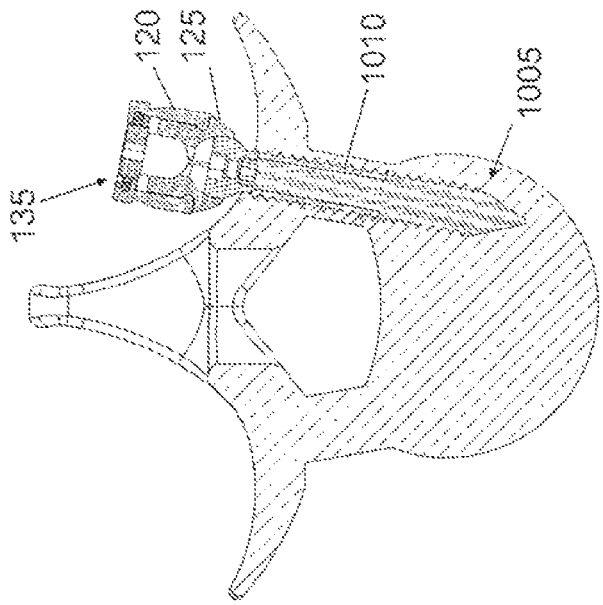

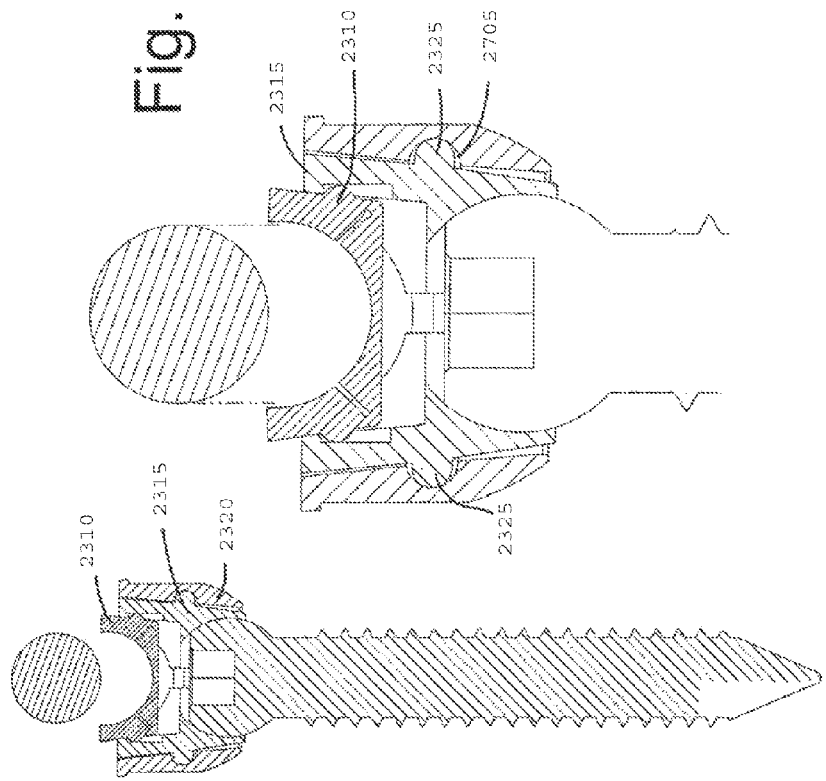

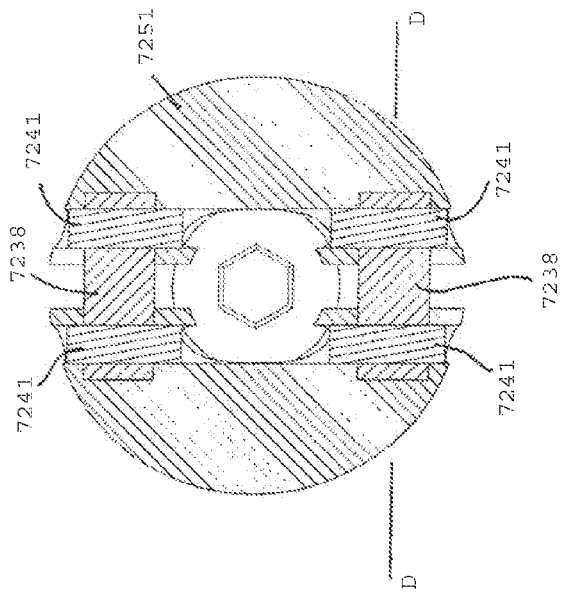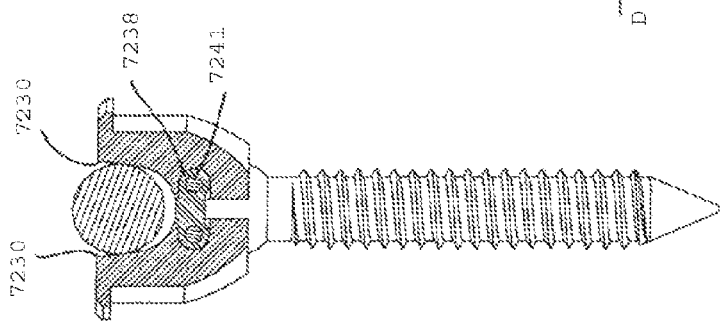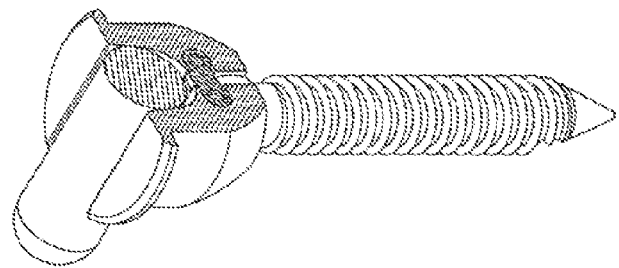

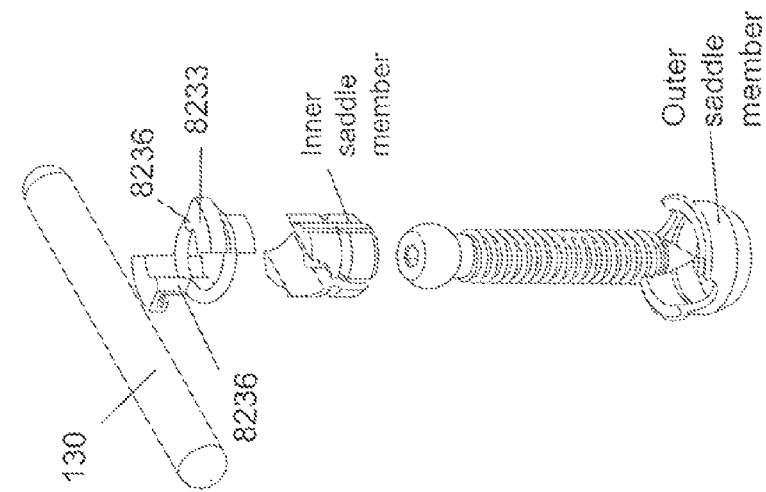
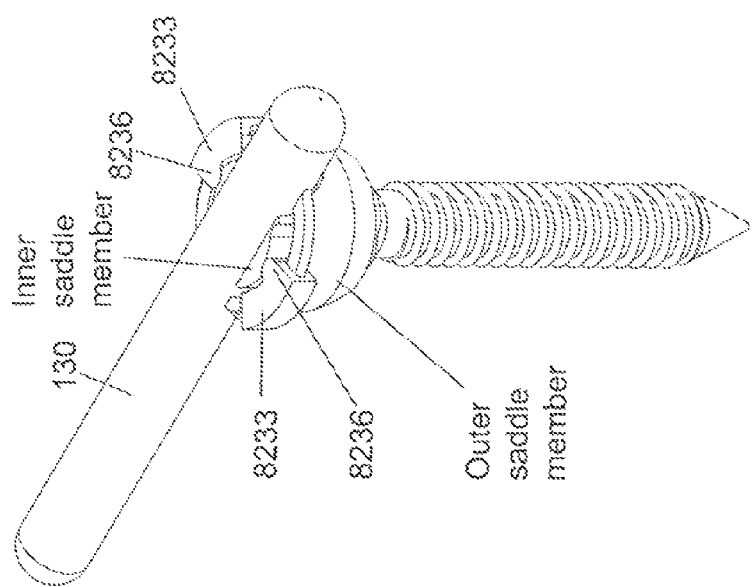

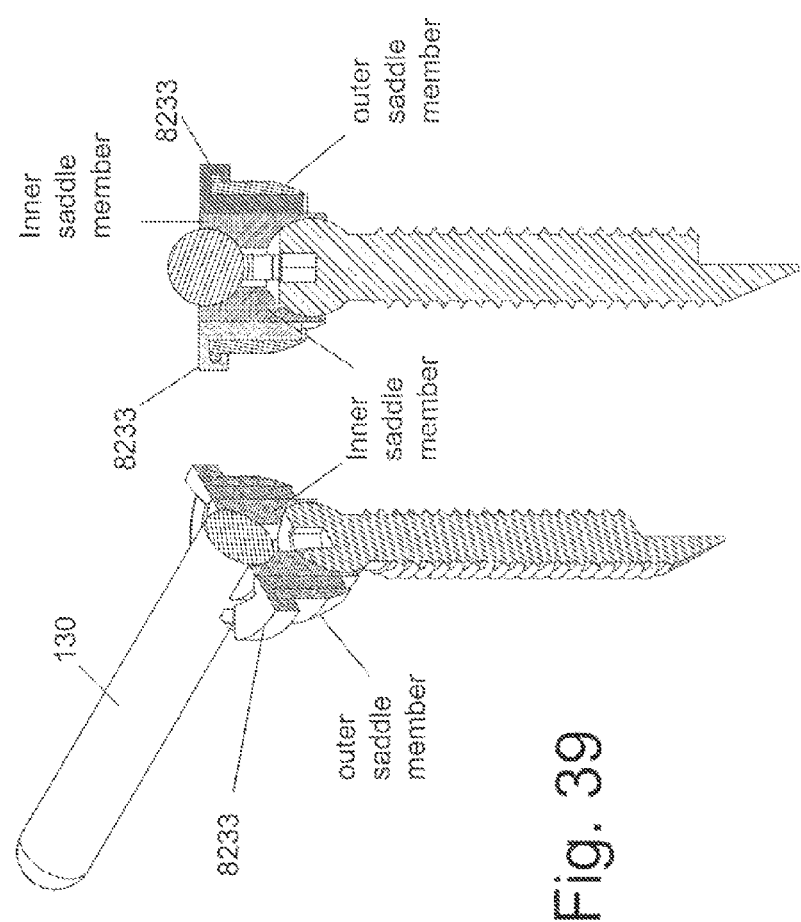

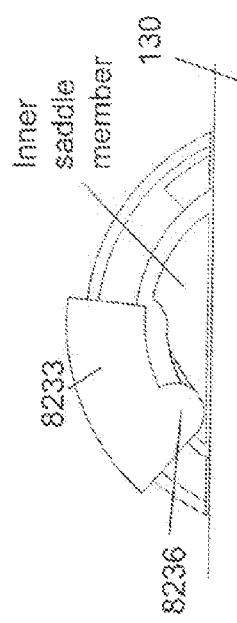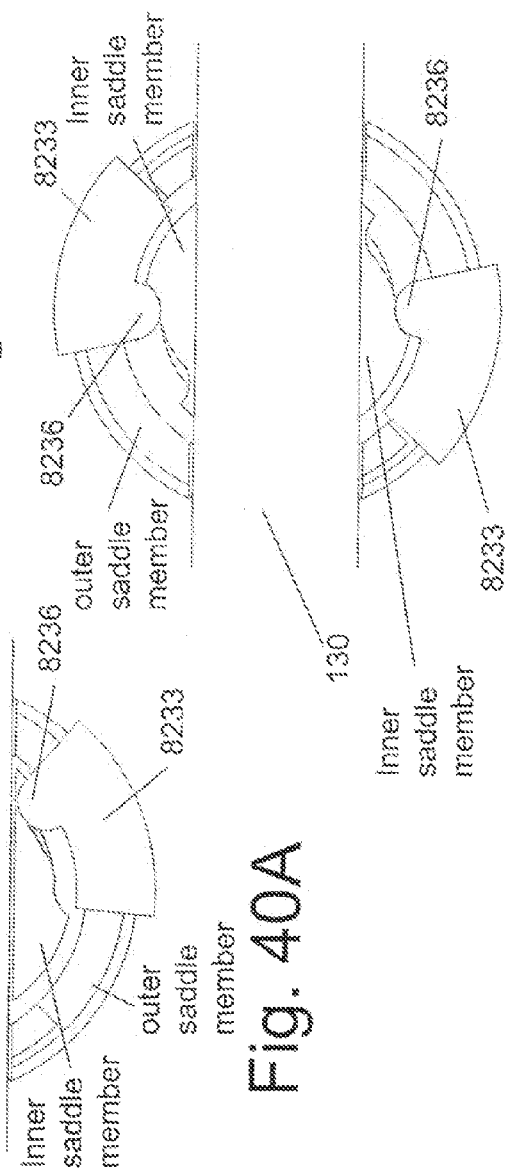

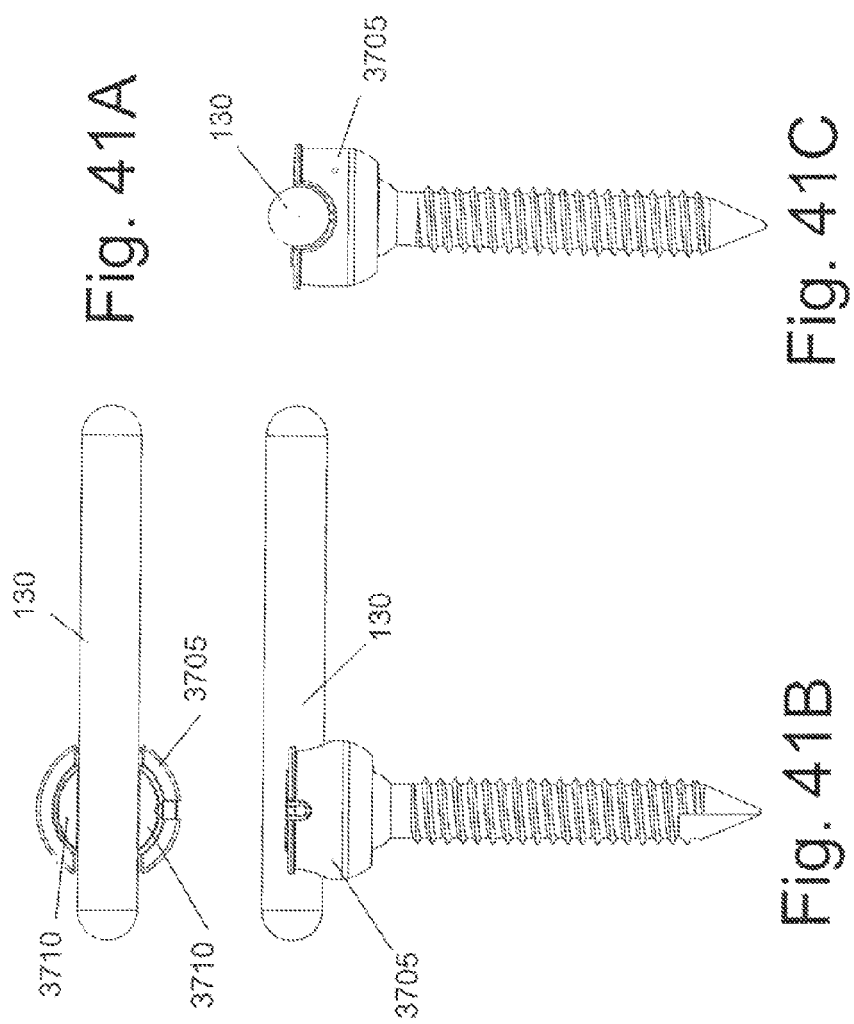

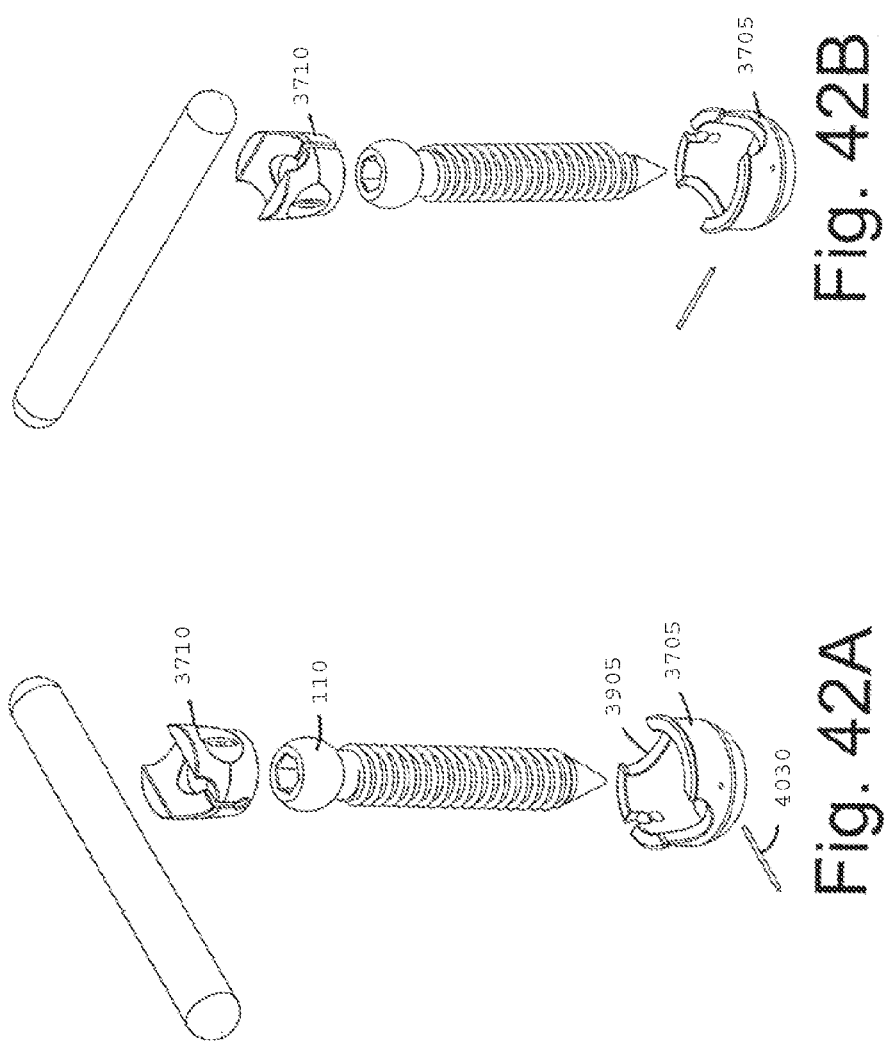

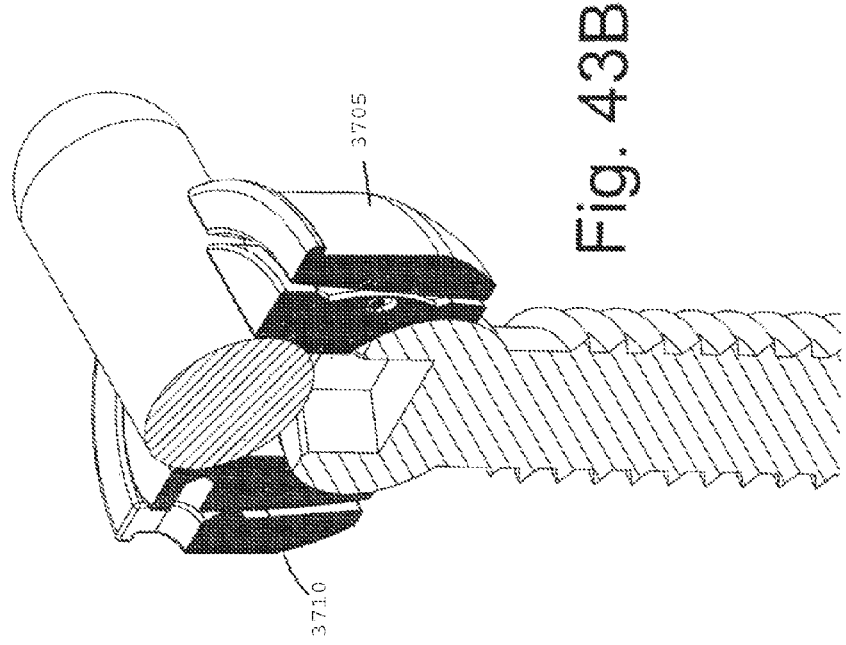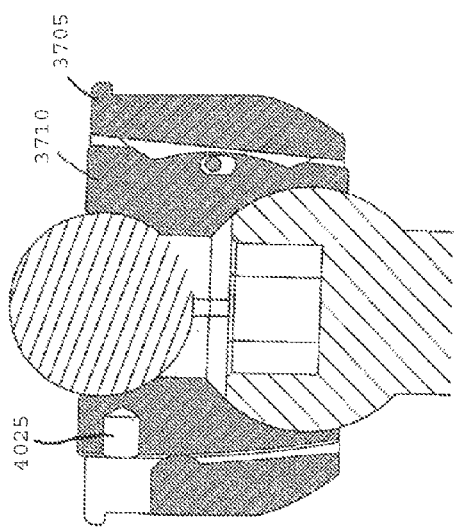

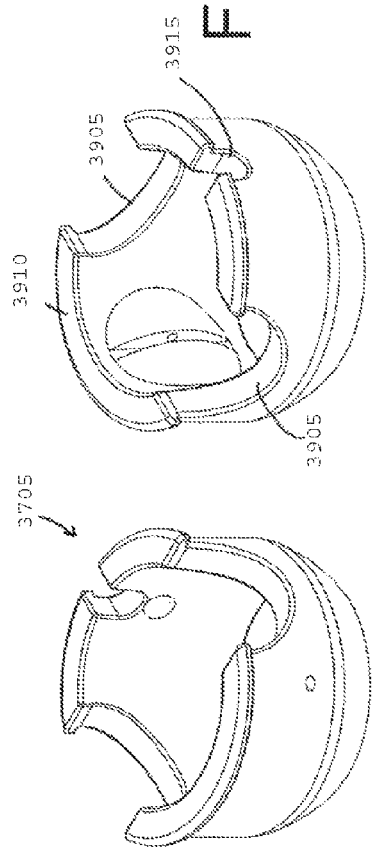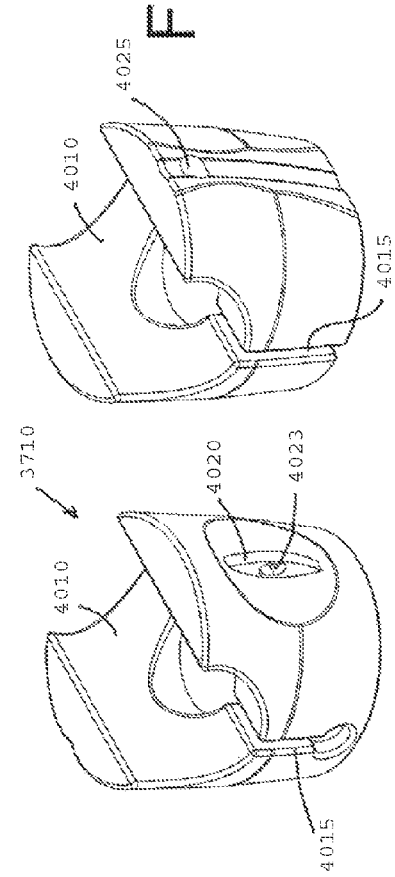

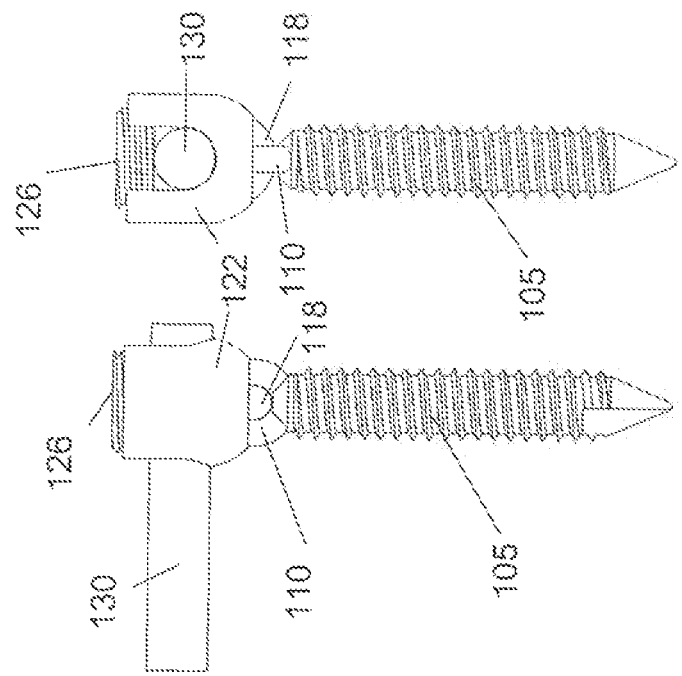
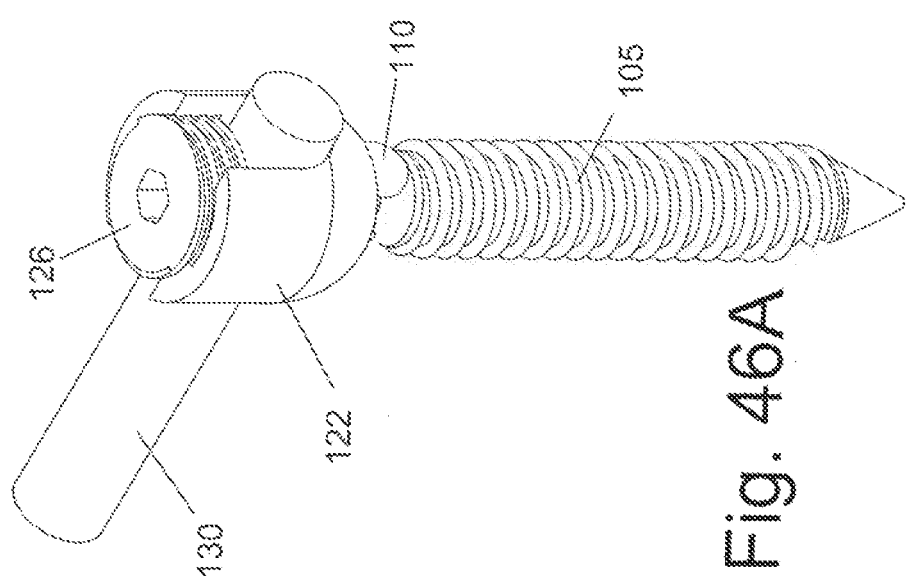
Fig. 46A
Fig. 46B

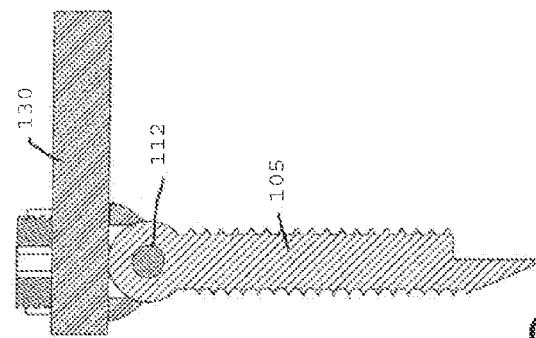
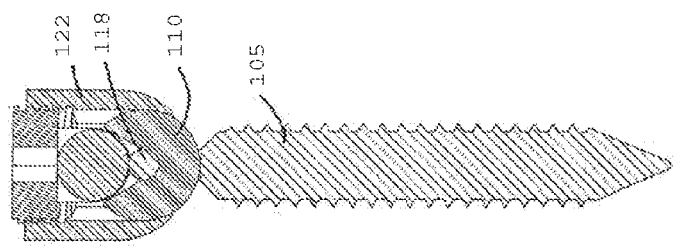
Fig. 48A
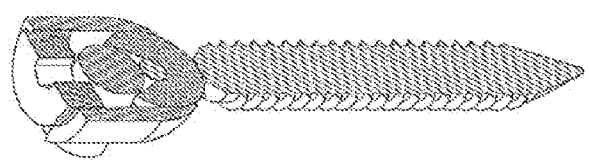
Fig. 48B

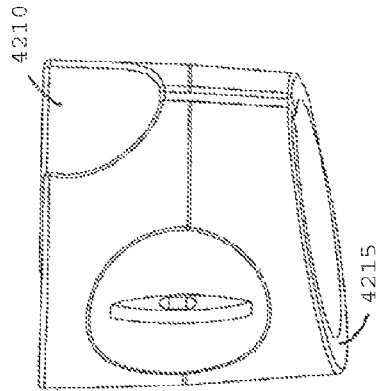
Fig. 49
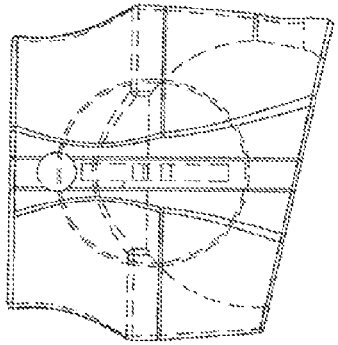
Fig. 50
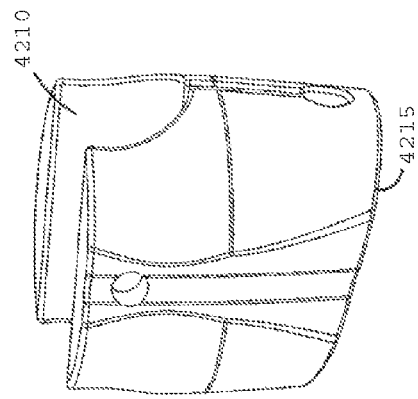
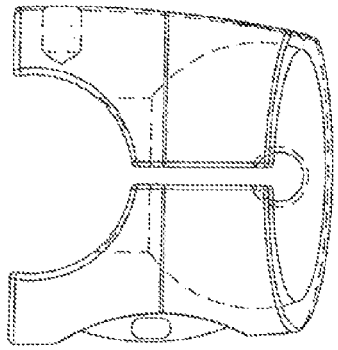

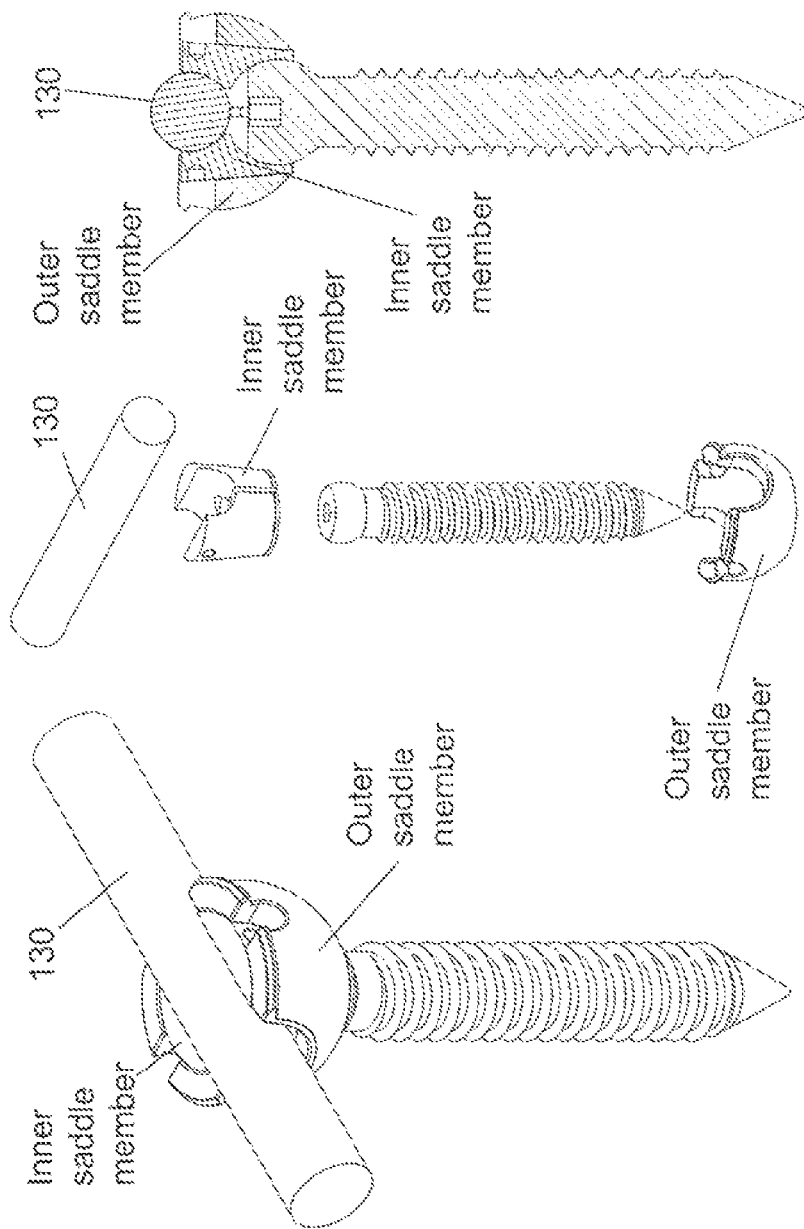

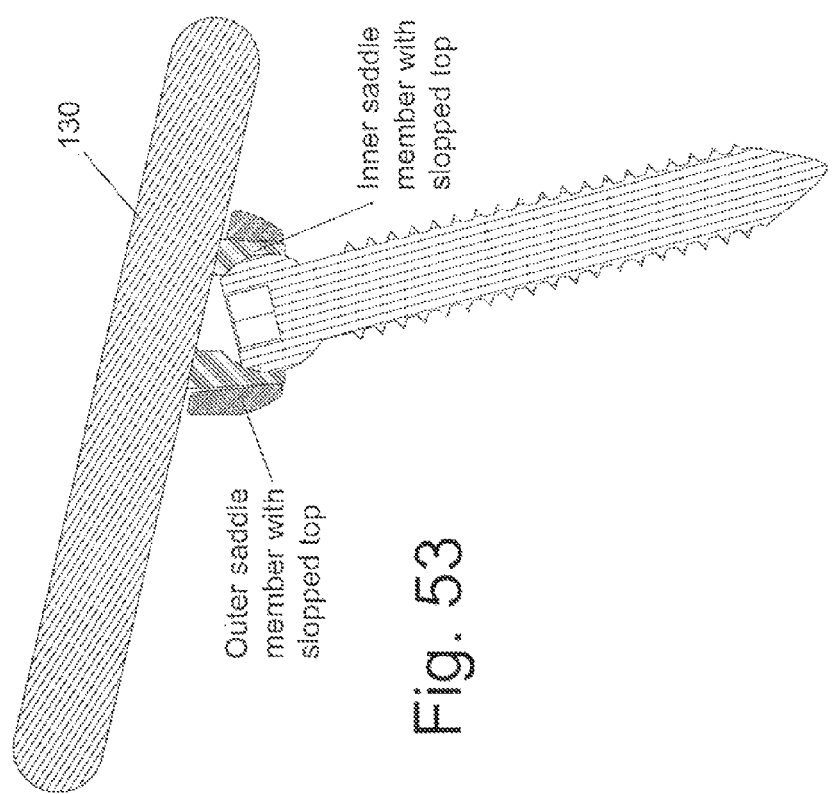

BONE SCREW SYSTEMS AND METHODS OF USE

REFERENCE TO PRIORITY DOCUMENT

This application claims priority of co-pending U.S. Provisional Patent Application Ser. No. 60/839,014, filed Aug. 21, 2006 and co-pending U.S. Provisional Patent Application Ser. No. 60/921,570, filed Apr. 3, 2007. Priority of the aforementioned filing dates is hereby claimed and the disclosures of the Provisional Patent Applications are hereby incorporated by reference in their entirety.

BACKGROUND

The present disclosure is related to orthopedic devices that are affixed onto skeletal segments. The implanted devices are used to adjust and maintain the spatial relationship(s) of adjacent bones. Depending on the implant design, the motion between the skeletal segments may be returned to normal, increased, modified, limited or completely immobilized.

Whether from degenerative disease, traumatic disruption, infection or neoplastic invasion, alterations in the anatomical relationships between the spinal vertebras can cause significant pain, deformity and disability. Spinal disease is a major health problem in the industrialized world and the surgical treatment of spinal pathology is an evolving discipline. The traditional surgical treatment of abnormal vertebral alignment and aberrant motion is the complete immobilization and bony fusion of the involved spinal segment. More recently, preservation of vertebral motion during the treatment of the spinal pathology has been the preferred strategy and many surgical techniques have been formulated to accomplish this treatment objective.

Regardless of whether the vertebral motion is abolished or preserved, many surgeons employ implantable orthopedic devices that adjust, align, support and/or maintain the spatial relationship(s) of the adjacent vertebral bones. The effectiveness of theses devices is vitally dependant on the adequacy of their fixation onto the underlying bone. Inadequate device fixation will effectively uncouple the device from the vertebral column and marginalize the beneficiary effects of the implant. Further, poorly anchored devices may damage the attached bone by fracturing and/or avulsing bone fragments at the attachment sites.

Screw fixation into the pedicle portion of the vertebral body has emerged as the most common method of device fixation onto the vertebral column. However, it is known that repeated loading and unloading of these screws will lead to screw loosening and eventual pull-out. Implantable devices that promote spinal fusion must bear load for the few months needed to produce bone graft maturation and solid vertebral fusion. In contrast, devices that preserve vertebral motion must bear the cyclical load of movement for the remainder of the patient's life. With the change in treatment strategy towards motion preservation, the integrity of the bone/device interface and the durability of the device fixation sites are emerging as major determinants of implant's functional life span.

There remains a significant need in the art for bone screw assemblies and methods of implantation that provide superior fixation onto the vertebral column. This need will increase further as surgeons widen the application of the motion preservation procedures.

SUMMARY

This application discloses bone screw systems that are adapted to provide superior anchor fixation onto the vertebral bones and to increase the resistance to anchor pull-out from the underlying bone.

In an embodiment, the distal bone screw segment of a bone screw system is driven into bone. In a first state, the assembly permits relative motion between its component parts in order to facilitate the placement and correct alignment of an inter-connecting rod that is used to couple multiple bone screw systems and/or other orthopedic devices. In a second state, the assembly provides relative immobilization between the assembly components and the inter-connecting rod. In an embodiment, the bone screw system is transitioned from a first state to a second state by the advancement of a locking member. Engagement of the locking member produces a downward force onto the interconnecting rod and a rotational movement of an inner housing member relative to an outer housing member about an abutment surface between the two housing members. With rotation, the inner housing member functions as a grasping claw that applies a compressive force onto a portion of the bone screw. In this way, the bone screw and the bone to which it is attached are retained by the assembly and affixed onto the rod.

In another embodiment, the force needed to transition the system from a first state to a second state is provided by the action of a locking instrument that is transiently used during system implantation but is not a component of the screw assembly. As before, engagement of the locking instrument produces a downward force onto the interconnecting rod and a rotational movement of an inner housing member relative to an outer housing member about an abutment surface between the two housing members. With rotation, the inner housing member functions as a grasping claw that applies a compressive force onto a portion of the bone screw and onto the rod. The force placed on the rod propels it into a fixed position relative to the inner housing and maintains it in that locked position even after removal of the locking instrument.

In another embodiment, the bone screw segment of the system contains a sub-segment that is partially composed of bone, bone substitute and/or a feature adapted to promote bone in-growth or establish a mineralized connection between the bone and the bone screw. In an embodiment, the sub-segment is intimately retained within a recess of the bone screw and provides a mineralized shoulder within the bone screw that will tenaciously resist screw migration. In other embodiments, the sub-segment forms a feature that may be actuated to protrude into the surrounding bone. These bone screw features may be used with any of the disclosed screw system designs.

In one aspect, there is disclosed an orthopedic anchoring system that is adapted to fixate implants onto the skeletal bone of a human or animal subject, comprising: a bone anchor that attaches onto bone and a receptacle that is adapted to mate with a second implant; an assembly including housing members coupled to the bone anchor, wherein the assembly transitions between a first state and a second state, wherein the first state permits relative motion between the anchor and the receptacle and the second state immobilizes the anchor relative to the receptacle and wherein transition from the first state to the second state requires non-linear movement between the housing members of the assembly; and a lock member that is contained within the assembly, wherein actuation of the lock member provides a force that causes the assembly to transition from the first state to the second state.

In another aspect, there is disclosed an orthopedic anchoring system that is adapted to fixate an implant onto the skeletal bone of a human or animal subject, comprising: a bone anchor that attaches onto bone and a receptacle that is adapted to mate with a second implant; an assembly including housing members coupled to the bone anchor, wherein the assembly transitions between a first state and a second state, wherein the first state permits relative motion between the anchor and the receptacle and the second state immobilizes the anchor relative to the receptacle and wherein transition from the first state to the second state requires non-linear movement between the housing members of the assembly; and a locking member coupled to the assembly wherein a force required to transition the assembly from the first state to the second state must be provided by an external instrument that is not contained within the assembly and wherein the assembly is capable of passively maintaining a locking force to maintain the assembly in the second state after removal of the external instrument that produced the force.

Other features and advantages will be apparent from the following description of various embodiments, which illustrate, by way of example, the principles of the disclosed devices and methods.

BRIEF DESCRIPTION OF THE DRAWINGS

FIGS. 2A-2C show top and side views of the system.

FIG. 3 shows the system in an exploded state.

FIG. 4 shows perspective and side cross-sectional views of the system.

FIG. 5 shows a lock nut assembly of the system in an exploded state.

FIG. 10 shows another embodiment of a bone screw system assembly in an exploded state.

FIG. 11A shows the bone screw system of FIG. 10 inserted into a pedicle segment of a vertebral body.

FIG. 11B illustrates an alternative method of screw fixation onto the vertebral pedicle.

FIG. 12 shows the bone screw system at the time of screw assembly removal. The screw head and the remainder of the locking assembly have been removed.

FIGS. 15A and 15B show the bone screw system of FIG. 13 mounted into bone with the shank assembly in the relaxed state and the engaged state, respectively.

FIGS. 24 and 25 show cross-sectional views of the assembled system prior to rod placement.

FIG. 36A shows vertical sectional views of the device of FIG. 35 taken through a hinge member.

FIG. 36B shows a horizontal sectional view of the device of FIG. 35 taken through the hinge members.

FIGS. 38A and 38B show an additional embodiment in perspective and exploded views, respectively.

FIG. 39 shows cross-sectional views of the system.

FIGS. 40A and 40B show top views of the device of FIG. 38 in the unlocked and locked configurations, respectively.

FIGS. 41A to 41C show views of another system embodiment.

FIGS. 42A and 42B show exploded views of the embodiment of FIG. 41.

FIGS. 43A and 43B show cross-sectional views of the device of FIG. 41.

FIGS. 44A and 44B illustrate the outer and inner saddle members, respectively.

FIGS. 46A and 46B illustrate an additional embodiment.

FIGS. 48A and 48B show cross-sectional views of the device in FIG. 46.

FIG. 49 shows side views of an alternative inner saddle member.

FIG. 50 shows the cross-sectional features using phantom lines.

FIGS. 51A-51C show perspective, exploded and cross-sectional views of an illustrative embodiment.

FIG. 53 shows an alternative embodiment that biases the bone screw towards a preferred direction.

DETAILED DESCRIPTION

Figure 1:
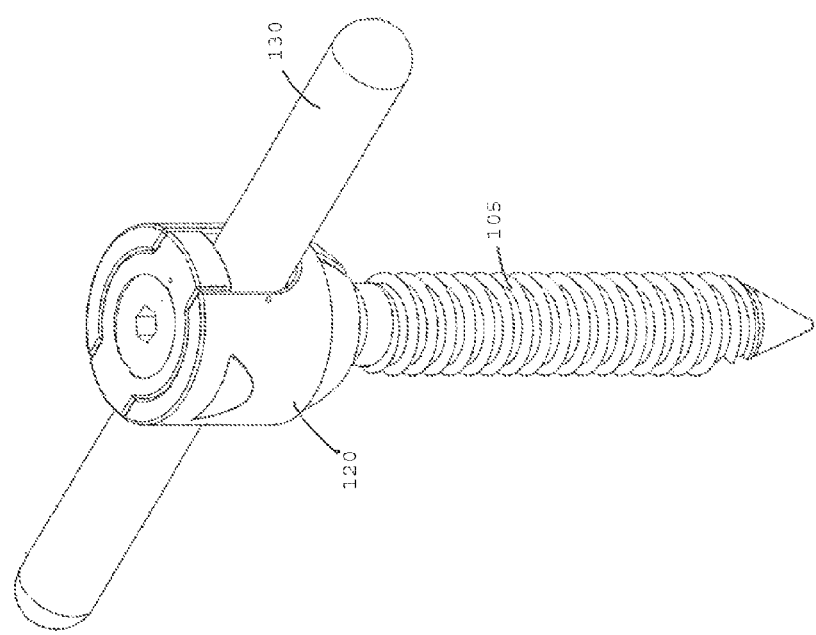
FIG. 1 shows perspective views of a first embodiment of a bone screw system.

FIG. 1 shows perspective views of a first embodiment of a bone screw system. FIGS. 2A-2C show top and side views of the system. FIG. 3 shows the system in an exploded state and FIG. 4 shows perspective and side cross-sectional views of the system. The system includes a bone screw having a shank 105 that extends from a head 110. The shank 105 can be screwed into bone. In the assembled system, the head is seated within a saddle assembly that includes an outer saddle member 120 that removably couples to a pair of inner saddle members 125. The inner saddle members 125 fit partially inside the outer saddle member 125 with a portion of the inner saddle members 125 protruding downwardly therefrom. The inner saddle members 125 collectively form a seat that receives the screw head 110, as shown in FIG. 4. The inner saddle members 125 also form a receptacle or seat that receives a second implant such as a rod 130, which also sits in a slot in the outer saddle members 120. As shown in FIG. 4, the outer saddle member 120 mates with the inner saddle members 125 via a complementary-shaped interface therebetween. The interface holds the inner saddle and outer saddle in a connected relationship that can be tightened and locked via a lock nut assembly, which is described below with reference to FIGS. 3 and 5. When the lock nut assembly is fully tightened, the rod 130 and screw head 110 are immobilized relative to the saddle assembly.

With reference to FIG. 3, the system further includes a lock nut assembly 135 that can be used to immobilize the screw head 110 and rod 130 relative to the saddle assembly, as described in detail below. The lock nut assembly 135 fits within and mates with an interior portion of the outer saddle member 120, as shown in FIG. 1.

FIG. 5 shows the lock nut assembly 135 in an exploded state. The lock nut assembly 135 includes an outer component 505, an inner component 510, and an annular or partially annular ring 518. The outer component 505 has a pair of laterally-extending wings 515 that are adapted to fit within the slots in the outer saddle member 120, as shown in FIG. 1. The outer component 505 also has a threaded bore 520 that is sized to receive the complementary-shaped inner component 510 which can be a locking nut, as described below. An annular groove or slot 525 is located on the wall of the bore 520 wherein the slot 525 is sized and shaped to receive the ring 518, as described more fully below.

Figure 7:
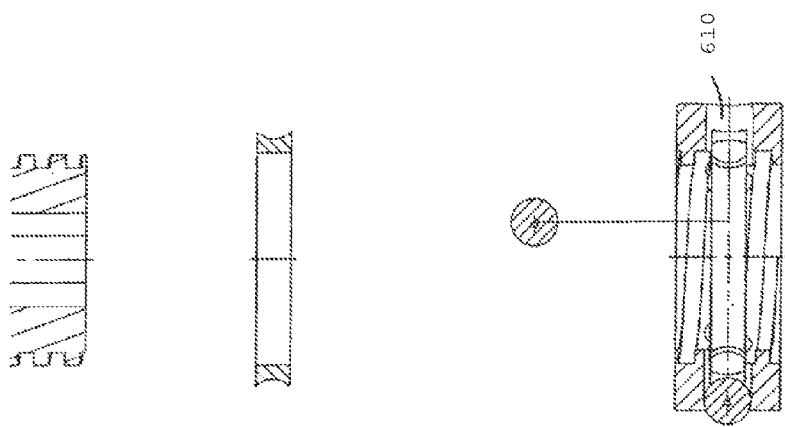
FIGS. 6 and 7 show perspective and cross-sectional views of the exploded lock nut assembly.
Figure 6:
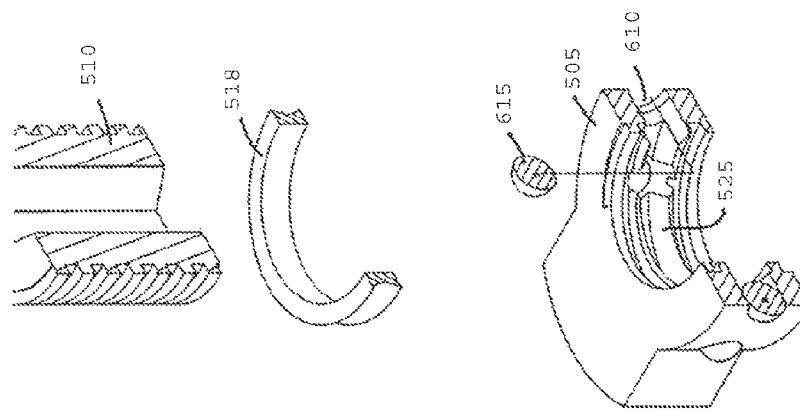

FIGS. 6 and 7 show perspective and cross-sectional views of the lock nut assembly in an exploded state. A plurality of radial-extending bore holes 610 are interspersed around the circumference of the threaded bore 520 of the outer component 505. The bore holes 610 form openings in the slot 525 of the bore 520 and in the exterior of the outer component 505. A spherical ball 615 is movably positioned within each of the bore holes 610. The balls 615 are sized and shaped relative to the bore holes 610 such that the balls 615 can move along the length of the bore holes 610 but cannot be moved out of the bore holes 610.

The ring 518 is biased toward an enlarged state. The ring 518 can be compressed to a size that permits the ring 518 to be inserted into the bore 520 of the outer component 505 and into the annular slot 525. When the lock nut assembly 135 is in an assembled state, the ring is positioned within the slot 525. The ring 518 expands radially outward within the slot 525 to force the balls 615 toward an extended position wherein at least a portion of each of the balls 615 protrudes outside of the outer component 505, as shown in FIG. 7. The compressible nature of the ring 518 permits the balls 610 to move radially inward in response to inward forces on the balls, unless the ring 518 is prohibited from being compressed, as described below. The assembled lock nut assembly 135 also includes the inner component 510, which is at least partially threaded into the bore 520 of the outer component 505. In this manner, the lock nut assembly 135 is essentially a unitary assembly that can be easily handled and manipulated.

In assembly, the inner saddles 125 are coupled to the outer saddle 120 with the head 110 of the bone screw seated in the inner saddle 120. The device is maintained in the assembled configuration by the action of assembly pins 126 and given to the surgeon as a unitary device. In use, screw 105 is driven into the underlying bone. Inter-connecting rod 130 is then lowered into the slot in the outer saddle 120 such that the rod 130 is seated within inner saddle members 125. After rod 130 is properly positioned, lock nut assembly 135 is then lowered into the outer saddle 120. Although the balls 615 are biased outward by the ring 518, the inner aspect of the outer saddle 120 pushes the balls 615 and the compressible ring 518 inward as the lock nut assembly 135 is advanced into the outer saddle 120. The lock nut assembly 135 is lowered until the balls 615 reach an annular groove 405 (FIG. 4) in the inner aspect of the outer saddle 120. At this point, the ring 518 forces the balls to snap into the groove 405. The balls interface with the groove to retain the lock nut assembly 135 in the outer saddle 120. At this stage, the rod 130 and the screw head 110 are movably positioned relative to the saddle assembly and the rod position can be adjusted further. This feature permits the surgeon to apply a compressive or distractive force between individual screw systems before the systems are locked.

Figure 8:
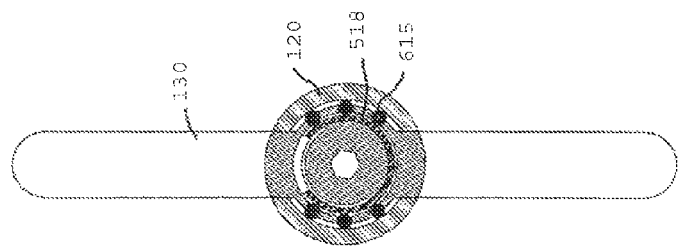
FIG. 8 shows a top, cross-sectional view of the immobilized screw system that is taken through the lock nut assembly.

After the rod 130 is appropriately positioned, the screw system is immobilized by advancing the inner component 510 of the lock nut assembly 135 deeper into the outer components 505. As component 510 is advanced, it covers the inner aspect of the ring 518 so that the ring is no longer compressible. When the ring 518 becomes incompressible, the balls 615 are locked in the extended position within the grove of the outer saddle member. As the inner component 505 is advanced further, it exerts a downward force onto rod 130 and advances the rod relative to inner saddle member 125. The side walls of the rod-receiving potion of inner saddle member 125 are inclined, as shown in FIG. 4, so that the upper portions of the side walls are separated by a greater distance than the lower portions of the side walls. Because of this wall configuration, advancement of rod 130 creates a distractive force between the side walls of the rod-receiving potion of inner saddle member 125 and produces rotation (i.e., non-linear movement) of each inner saddle member 125 relative to outer saddle member 120 about the abutment protrusions 129 of the outer saddle member. With rotation, the inferior segments of the inner saddle members are driven towards one another and they collectively function as a grasping claw that applies a compressive force onto head 110 of the bone screw. In this way, the assembly is rigidly immobilized relative to rod 130. A longitudinal cross-sectional view of the immobilized device is shown in FIG. 4. A horizontal cross-sectional view of the locking nut assembly 135 is shown in FIG. 8. As illustrated, ring 518 retains balls 615 in the extended state and, in the locked state, nut 510 prevents the compression of ring 518.

Figure 9:
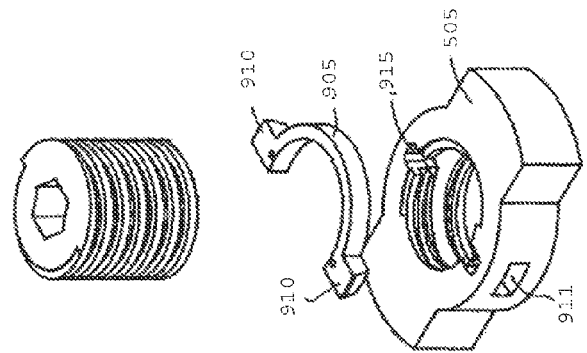
FIG. 9 shows another embodiment of a lock nut assembly.

FIG. 9 shows another embodiment of the lock nut assembly 135. In this embodiment, the ring and balls of the previous embodiment are replaced by a snap ring 905 that is biased toward a radially-expanded state. The snap ring 905 includes at least one protrusions 910 that fits into holes 915 in the outer member 505. The protrusions have sloped bottom surfaces such that the protrusions 910 are automatically forced inward as the lock nut assembly is lowered into the outer saddle 120. The protrusions 910 snap into the groove in the inner aspect of the outer saddle 120 in the same manner that the balls of the previous embodiment snap into the groove. Holes 911 are adapted to accept a removal instrument, wherein the instrument can exert a compressive force onto the ring 905 and remove the lock nut assembly 135. The illustrated lock nut assemblies provide retractable members that transiently retract on insertion to pass a screw assembly protrusion and then expand to occupy a position within a screw assembly indentation. In this way, the lock nut assembly forms an interference feature that retains the rod within the screw system assembly and, with advancement of the central nut of the lock nut assembly, rigidly locks the screw system components. It should be appreciated that this functional mechanism can be provided by lock nut assemblies that vary in structure from the illustrated embodiments.

FIG. 10 shows another embodiment of a bone screw system in an exploded state. In this embodiment, the saddle and lock nut assembly features are similar or the same as in the previous embodiment but the bone screw has been modified in order to provide superior bone fixation. The bone screw is formed of multiple components, including a multi-piece shank assembly that removably couples to the head 110. The shank assembly includes an inner shank member 1005 that at least partially inserts into an internal bore in the outer shank member 1010. The inner shank member 1005 has an upper region 1015 that slidably mates into the bore within the outer shank member 1010, and a lower region 1020 that is threaded for locking onto bone. Upper region 1015 of inner shank 1005 has protrusion 1016 that cooperatively fits within a complimentary indentation or slit within outer shank member 1010. Protrusion 1016 functions to prevent rotation of outer member 1010 relative to inner shank member 1005. Outer member 1010 is preferably at least partially made of bone, bone graft substitute and/or a feature adapted to promote bone in-growth or establish a mineralized connection between outer member 1010 and the surrounding vertebral bone. A coupler 1025, such as a threaded coupler, removably mates with the head 110 in the assembled device, as illustrated in FIG. 11A, which shows the bone screw system inserted into a pedicle segment of a vertebral body. The outer shank member 1010 is intimately applied to the upper region 1015 of inner shank 1005 so that, with bone in-growth into member 1010, a mineralized shoulder is formed within the substance of the bone screw. The mineralized segment will tenaciously resist screw migration and significantly increase the pull-out resistance of the screw.

FIG. 11A illustrates screw placement within the pedicle portion P of the vertebra. Biomechanical research has shown that the pedicle P forms an optimal bone attachment site for bone screws and other orthopedic devices. As with other segments of bone, the pedicle has a tough outer wall and a more spongy interior that is marrow-like in consistency. The pedicle is substantially cylindrical and roughly forms a circular or elliptical outline in coronal cross-section. Engagement of at least a portion of the tough outer wall increases the strength of fixation. Fixation can be additionally enhanced by the "capture" of the outer wall of the pedicle (along the long axis) within a segment of the bone screw. This fixation method may be accomplished in several ways. In FIG. 11B, a pedicle is captured between a distal and a proximal protrusion segment of a bone screw. Alternatively, as shown in FIG. 11A, a bone screw may have an intermediate member that is captured between two segments of the bone screw, wherein the intermediate member forms a mineralized connection with the surrounding bone. In the latter embodiment (FIG. 11A), the tough outer pedicle surface is essentially extended into the substance of the bone screw by the action of the mineralized connection with the intermediate member.

After the mineralized connection has been established between a screw segment and the bone, the screw assembly can still be removed, when desired, by removal of the proximal segment—as illustrated in FIG. 12. The distal screw is then attached to a bone drill and a ring of bone is cut around the screw segment that remains embedded in the vertebral bone. After cutting the mineralized connection, the retained screw segment can be backed-out without difficulty.

In additional embodiments, the outer shank member 1010 of the bone screw can be actuated to change configuration. The inner shank member 1005 may be configured in one of various ways such that, upon actuation, it can alter the structural configuration of the outer shank member. For example, in an embodiment illustrated in FIGS. 13 to 15, actuation of the screw system causes the outer shank member 1010 to expand outward and into the surrounding bone.

Figure 13:
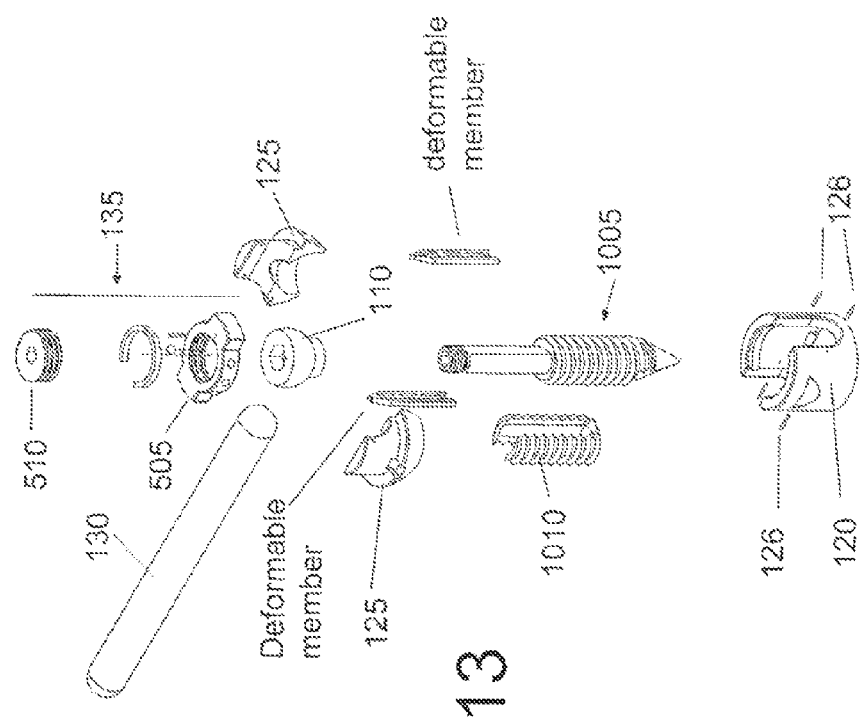
FIG. 13 shows another embodiment of a bone screw system assembly in an exploded state.
Figure 14B:
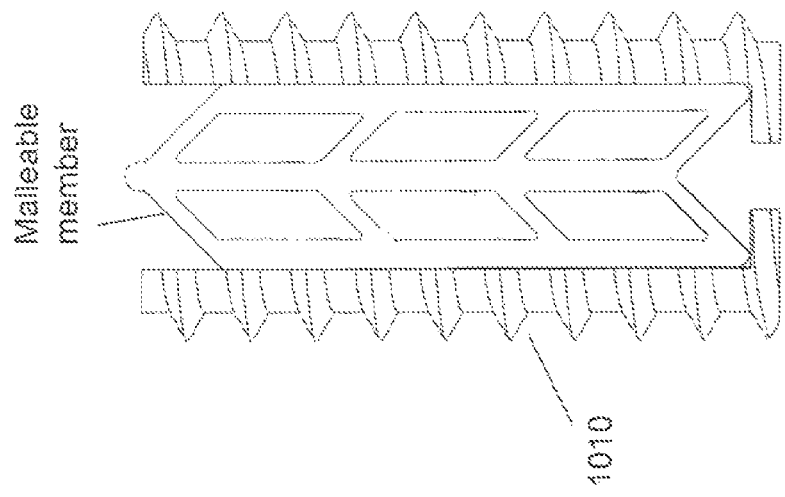
FIGS. 14A and 14B show an exemplary embodiment of an outer shank member in a relaxed state and an engaged state, respectively.
Figure 14A:
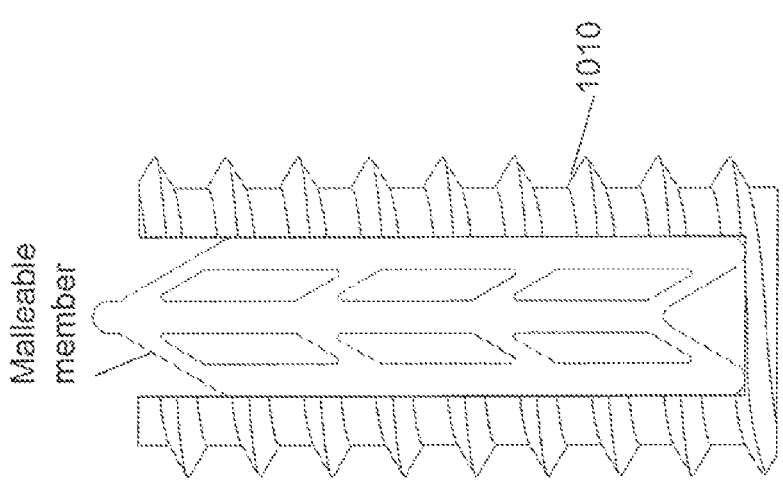

FIG. 13 shows an exemplary embodiment, wherein the outer shank member is composed of a central member that is preferably at least partially made of bone, a bone graft substitute and/or a feature adapted to promote bone in-growth or establish a mineralized connection between outer member 1010 and the surrounding vertebral bone. At least one defect is found in member 1010 wherein a deformable member is housed. FIG. 14A shows member 1010 with the deformable member in a first, un-deployed state while FIG. 14B shows the deformable member in a second, deployed state. Note that the residual connecting bridge at the inferior aspect of member 1010 is broken by the deployment of the deformable member from the first to second state. The deformable member is actuated between the first and second states by the rotation of head 110 relative to shank 1005. This action shortens the height of the deformable member and increases its width, thereby producing the configuration change of member 1010 that is shown in FIG. 14B. FIGS. 15A and 15B show cross-sectional views of the screw system of FIG. 13 implanted within a vertebra, wherein FIG. 15A shows the deformable member in a first, un-deployed state and FIG. 15B shows the deformable member in a second, deployed state.

Figure 16B:
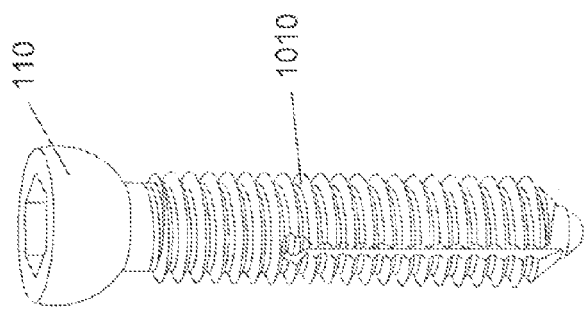
FIGS. 16A and 16B show another embodiment of an inner shank member and outer shank member.
Figure 16A:
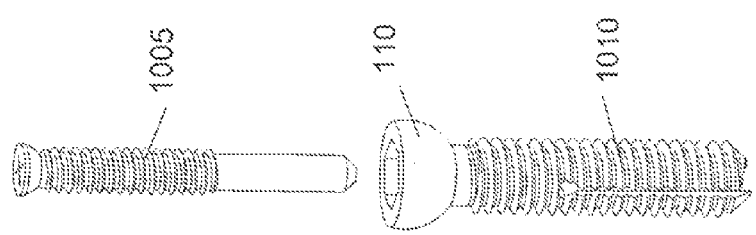
Figure 18A:
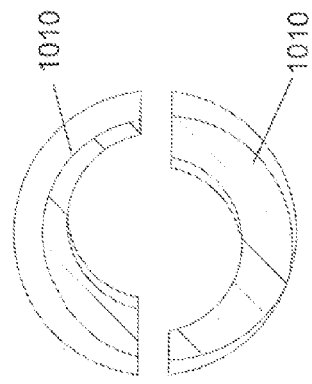
FIGS. 18A and 18B show a cross-sectional view of the outer shank member before and after insertion of the inner screw shank member, respectively.
Figure 18B:
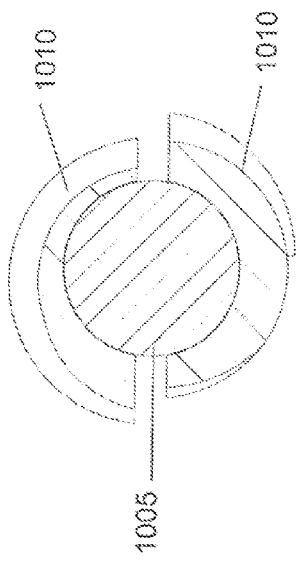
Figure 17:
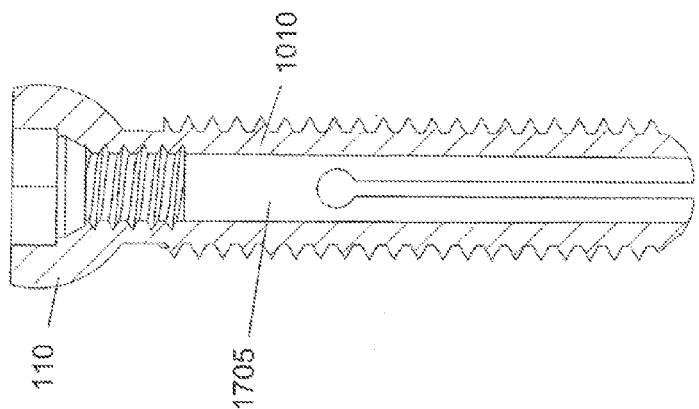
FIG. 17 shows a cross-sectional view of the outer shank member.

FIGS. 16A and 16B show another embodiment of an inner shank member and outer shank member. In this embodiment, the outer shank member 1010 has a head 110 with an opening 1105 that receives the inner shank member 1005. The inner shank member 1005 fits within an internal bore in the outer shank member. FIG. 17 shows a cross-sectional view of the outer shank member 1010. The internal bore 1705 has an upper threaded region that mates with outer threads on the inner shank member 1005. The lower region of the bore 1705 is non-threaded. With insertion of the inner shank member 1005 into the bore 1705, the configuration of the inner bore 1705 is forced to conform to that of the inner shank member 1005. This alters the outer configuration of the outer shank member 1010 such that it undergoes a shape change. FIGS. 18A and 18B show the structural configuration of the outer shank member before and after insertion of the inner shank member, respectively. FIG. 18A shows the outer shank member alone in the "relaxed" configuration while FIG. 18B shows the outer shank with the inner screw member in the "engaged" state. In the "engaged" configuration of the outer shank member, sections of the screw are propelled in pre-determined directions without an overall expansion of the screw or an increase in its size. This configuration change will increase the bone holding capability of the entire assembly and increase its resistance to pull-out.

Figure 20:
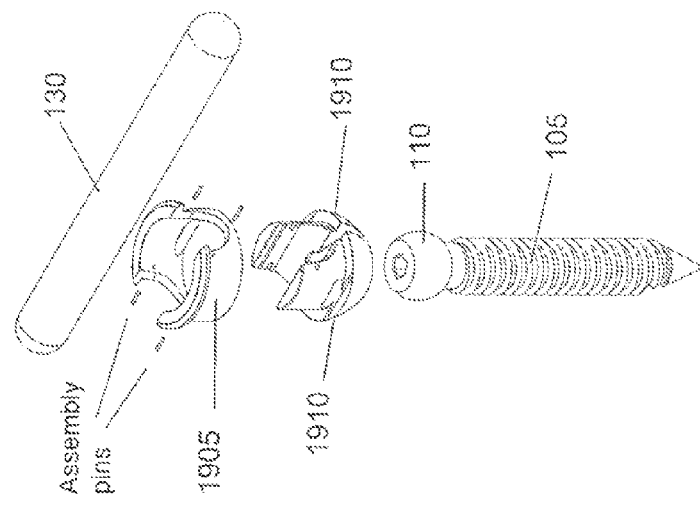
FIG. 20 shows an exploded view of the system of FIG. 19.
Figure 19:
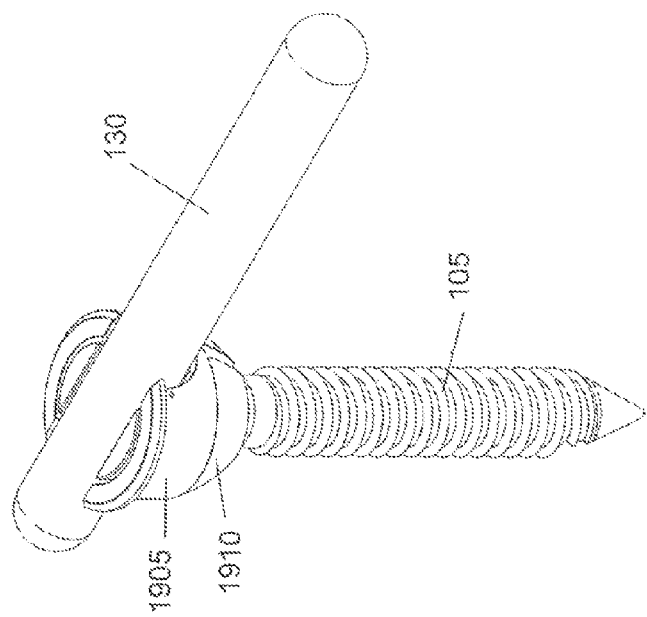
FIG. 19 shows a perspective view of another embodiment of a bone screw system.
Figure 21:
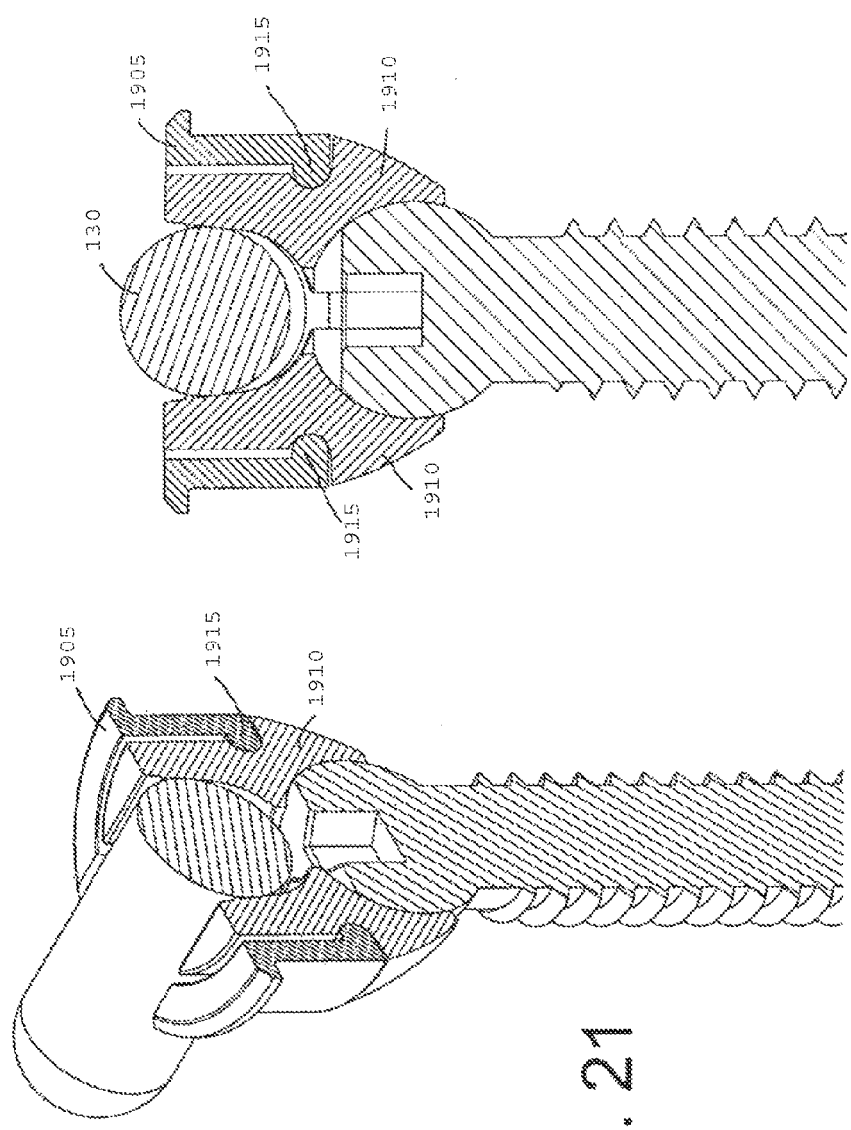
FIG. 21 shows perspective and cross-sectional views of the system of FIG. 19.

While the bone screw is mainly embedded in bone, the portion of the screw system that provides the locking feature rests above the bone and below the skin. As previously described, the force required to lock the assembly is provided by lock nut assembly 135. In order to reduce the overall height of this segment and lower the profile of the system, several embodiments are disclosed in which the force required to lock the assembly is provided by the action of a locking instrument that is transiently used during screw system implantation but is not a component of the screw assembly itself. FIG. 19 illustrates a perspective assembled and locked view of the current embodiment while FIG. 20 shows an exploded view of the system. FIG. 21 shows perspective and cross-sectional views of the system.

The system includes a bone screw having a shank 105 and a head 110. The head 110 sits in a saddle assembly that includes an outer saddle member 1905 which mates with a pair of inner saddle members 1910. The inner saddle members 1910 fit partially inside the outer saddle member 1905 with a portion of the inner saddle members 1910 protruding downwardly therefrom. The inner saddle members collectively form a seat that receives the screw head 110, as shown in FIG. 21. In use, the device is maintained in the assembled configuration by the action of assembly pins and given to the surgeon as a unitary device.

The inner saddle members also form a seat that supports the rod 130, wherein the side walls of the rod-receiving seat of the inner saddle members are inclined, as shown in FIG. 21, so that the upper portions of the side walls are separated by a greater distance than the lower portions of the side walls. Because of this wall configuration, advancement of rod 130 creates a distractive force between the side walls of the rod-receiving seat of inner saddle member and produces rotation of each inner saddle member relative to outer saddle member 1905 about the abutment protrusions 1915 of the outer saddle member. With rotation, the inferior segments of the inner saddle members are driven towards one another and they collectively function as a grasping claw that applies a compressive force onto head 110 of the bone screw. The locking force is provided by a separate implantation instrument (not shown) and the locking force is maintained even after the instrument is removed by ridged protrusions, indentations or other retaining features on the inner aspects of the rod-receiving seat of the inner saddle members.

Figure 23:
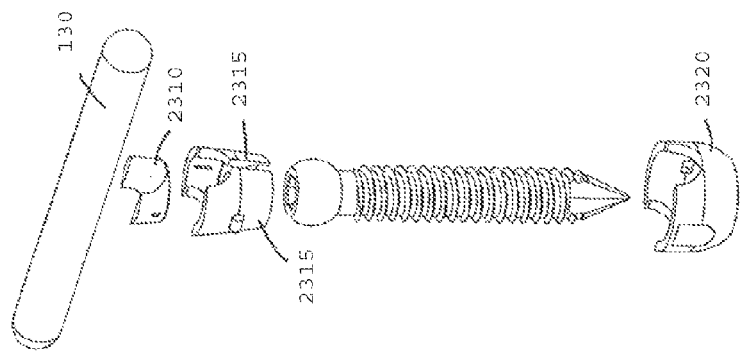
FIG. 23 shows the system in an exploded state.
Figure 22:
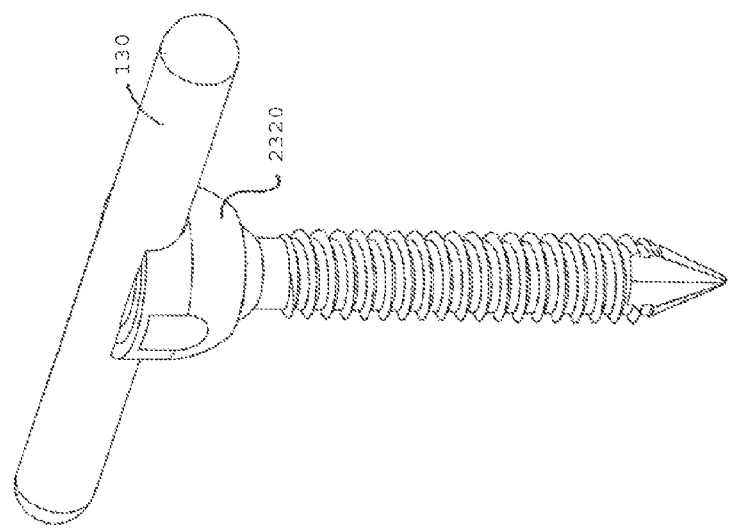
FIG. 22 shows another embodiment of a bone screw system.

FIG. 22 shows another embodiment of a bone screw system. FIG. 23 shows the system in an exploded state and FIG. 24 shows the system prior to rod placement. As in the embodiment of FIGS. 19-21, a locking nut is not employed in this embodiment. The system includes a bone screw with a head 110 that sits in a saddle assembly. The saddle assembly includes an inner saddle member 2310 having a seat that receives the rod 130. The saddle assembly further includes intermediate saddle members 2315 that collectively receive the inner saddle member 2310. The saddle assembly further includes an outer saddle member 2320 in which the intermediate saddle members 2315 can be positioned. In FIG. 24, the inner saddle member 2310 extends above the top surface of the screw. In this position, the upper aspect of the inner saddle member 2310 expands sufficiently to permit placement of the rod 130 into the inner saddle member 2310.

FIG. 25 shows an enlarged cross-sectional view of the device prior to rod placement. As mentioned, the head 110 is positioned in a seat collectively formed by the intermediate saddle members 2315. Each of the intermediate saddle members 2315 has a protrusion 2325 that mates with an opening in the outer saddle member 2320. The saddle assembly components are freely movable relative to the bone screw.

Figures 26, 27:
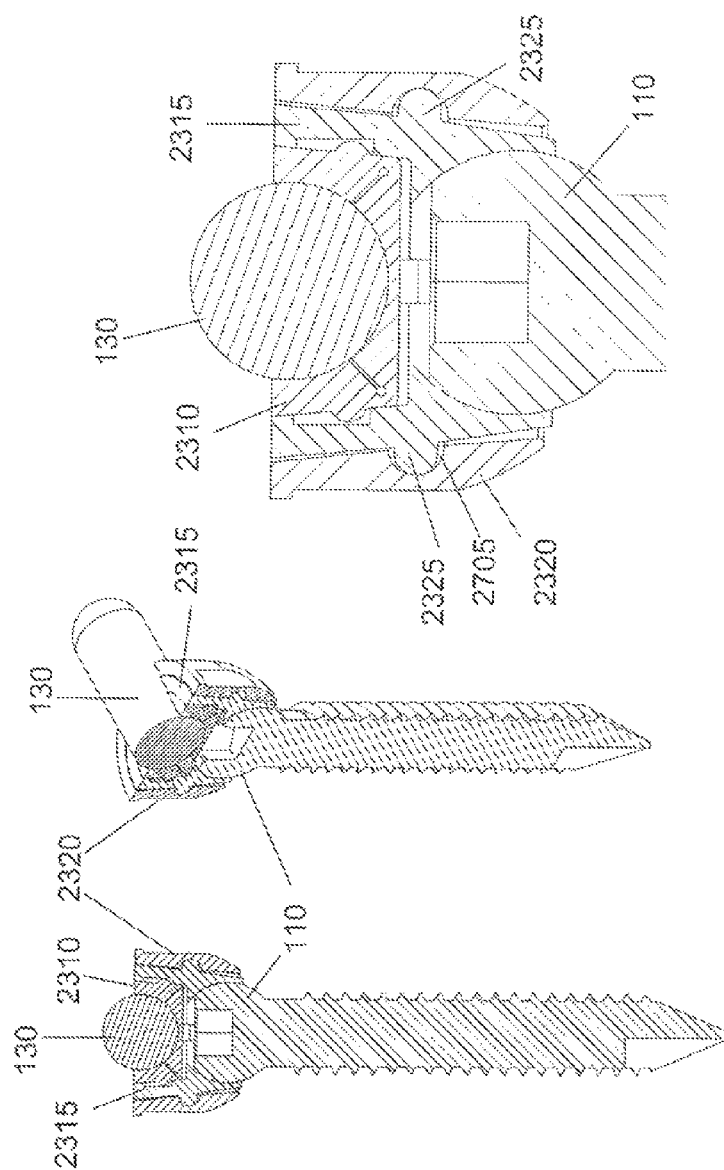
FIGS. 26 and 27 show cross-sectional views of the assembly after the rod is placed. The assembly is in the locked configuration.

The saddle assembly can be moved into a locked configuration by pushing the rod 130 downward into the inner saddle member 2310. FIGS. 26 and 27 show cross-sectional views of the assembly in the locked configuration. As a downward force is exerted onto the rod 130, the inner saddle member 2310 is pushed into a cavity within the confines of the intermediate saddle members 2315. As shown in FIG. 27, the protrusions 2325 are positioned within indentations 2705 of the outer saddle member 2320. The inner saddle member 2310 exerts an outward force onto the upper aspect of the intermediate members 2315. This causes the members 2315 to rotate relative to the center of the protrusion 2325 and push the bottom portion of each of the intermediate saddle members 2315 towards one another. In this way, the intermediate saddle members 2315 lock onto the spherical head 110 of the bone screw. A Morse taper exists between the outer surface of the inner saddle member 2310 and the inner surface of the members 2315 and provides a locking mechanism for the assembly. Alternatively, or additionally, one or more interference locks could be used to maintain the locking force after the locking instrument has been removed.

Figure 28:
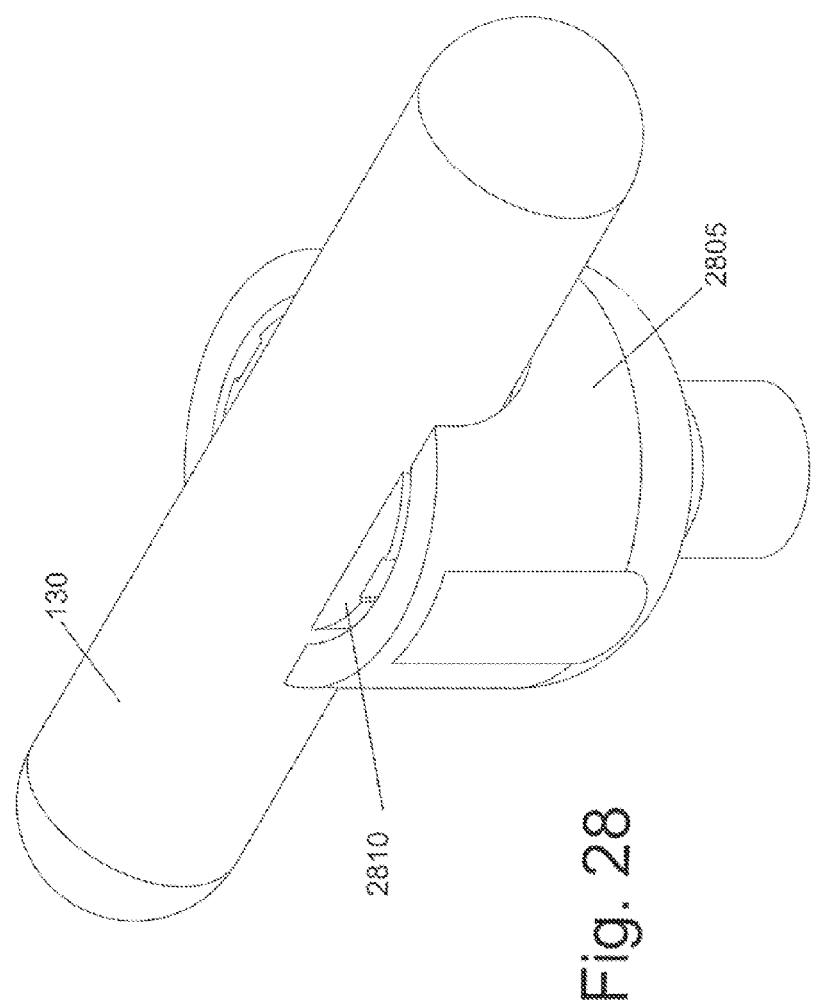
FIG. 28 shows another embodiment of a bone screw system.
Figure 29:
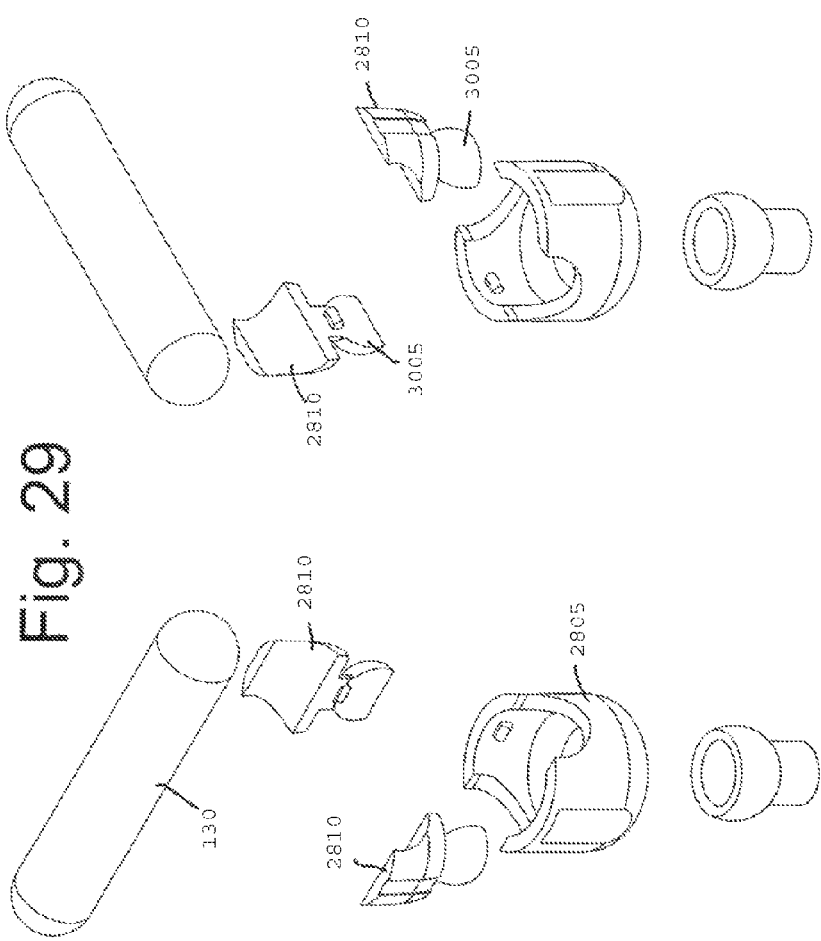
FIG. 29 shows the system in an exploded state.

FIG. 28 shows another embodiment of a bone screw system. FIG. 29 shows the system with a saddle assembly in an exploded state. As in some of the previous embodiments, a locking nut is not employed in this embodiment. The saddle assembly includes an outer saddle member 2805 and a pair of inner saddle members 2810 that are positionable within the outer saddle member 2805. An upper region of the inner saddle members 2810 collectively define a seat in which the rod 130 can be positioned. A lower region of the inner saddle members 2810 collectively form a spherical or partially spherical member 3005, as shown in the cross-sectional views of FIG. 30.

Figure 30:
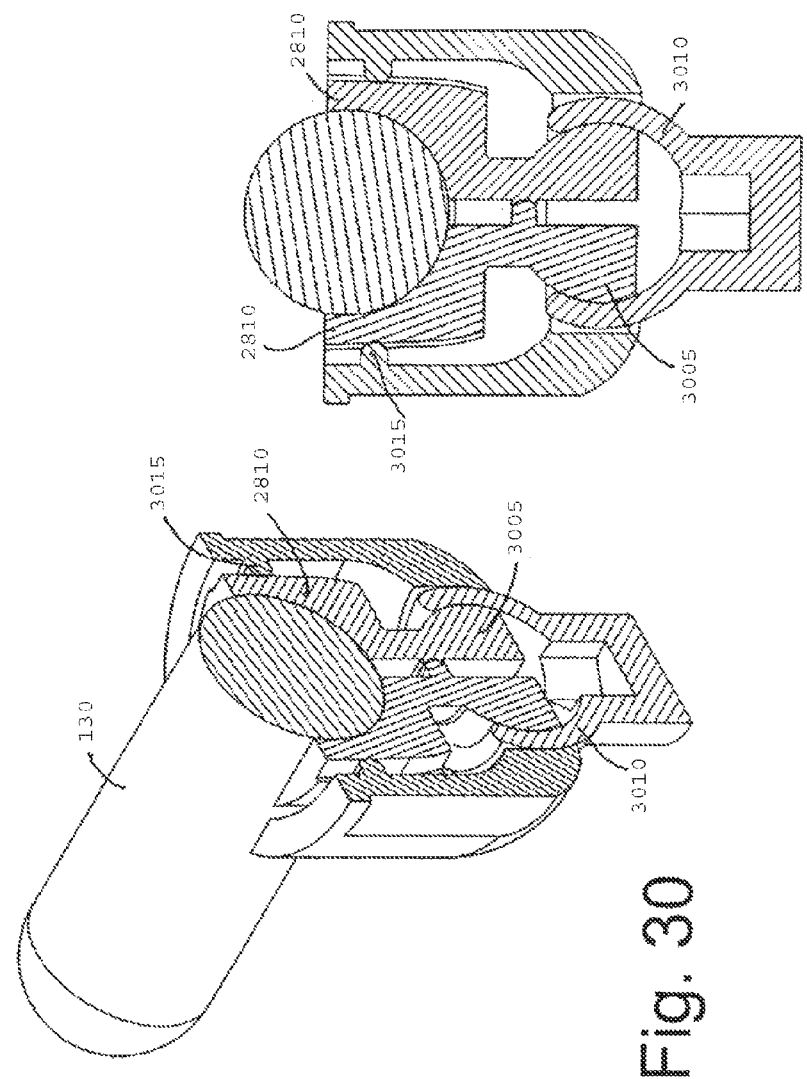
FIG. 30 shows perspective and side cross-sectional views of an upper region of the system.

With reference to the cross-sectional views of FIG. 30, the spherical member 3005 is rotationally positioned within the head 3010 of the bone screw. The head 3010 is sized and shaped so at the form a spherical cup or seat in which the spherical member 3005 of the inner saddle members 2810 is positioned. A pair of protrusions 3015 are located on the inner aspect of the outer saddle member 2805. The protrusions abut an outer aspect of the inner saddle members 2810, which are coupled to one another via a protrusion 3020.

The saddle assembly is locked by pushing the rod 130 downward into the inner saddle members 2810 and pulling the outer saddle member 2805 upward relative to the inner saddle members 2810. As the outer saddle member 2805 is pulled upward relative to the inner saddle members 2810, protrusions 3015 produce an inward directed force onto the outer walls of the inner saddle members 2810. The force causes the upper aspects of the inner saddle members 2810 to rotate about the center of protrusion 3020 so that the lower aspects of members 2810 move away from each other. The lower aspects of the inner saddle members 2810 forcefully constrain the bone screw head 3010 and immobilize the assembly.

Figure 32:
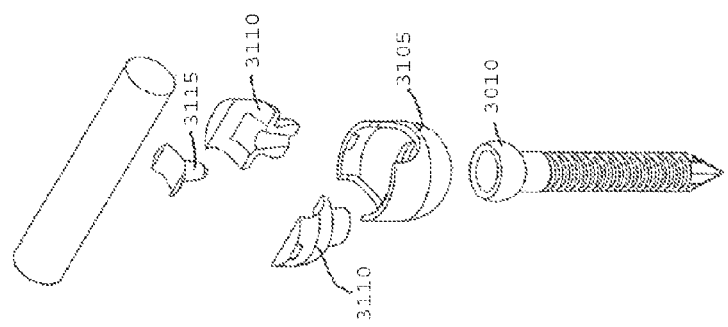
FIG. 32 shows the system in an exploded state.
Figure 31:
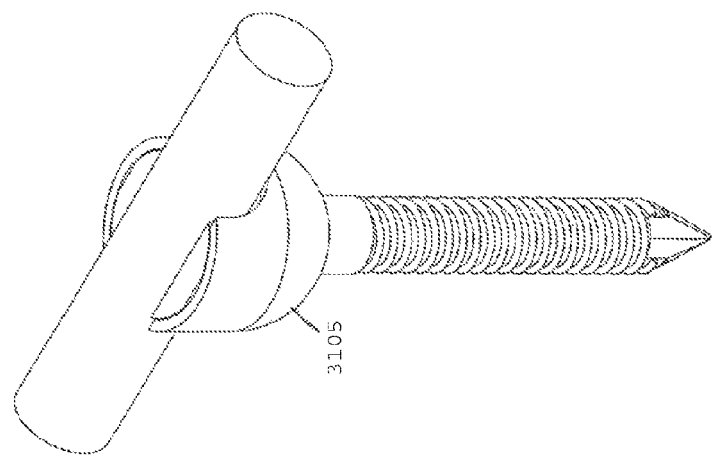
FIG. 31 shows another embodiment of a bone screw system.
Figure 33:
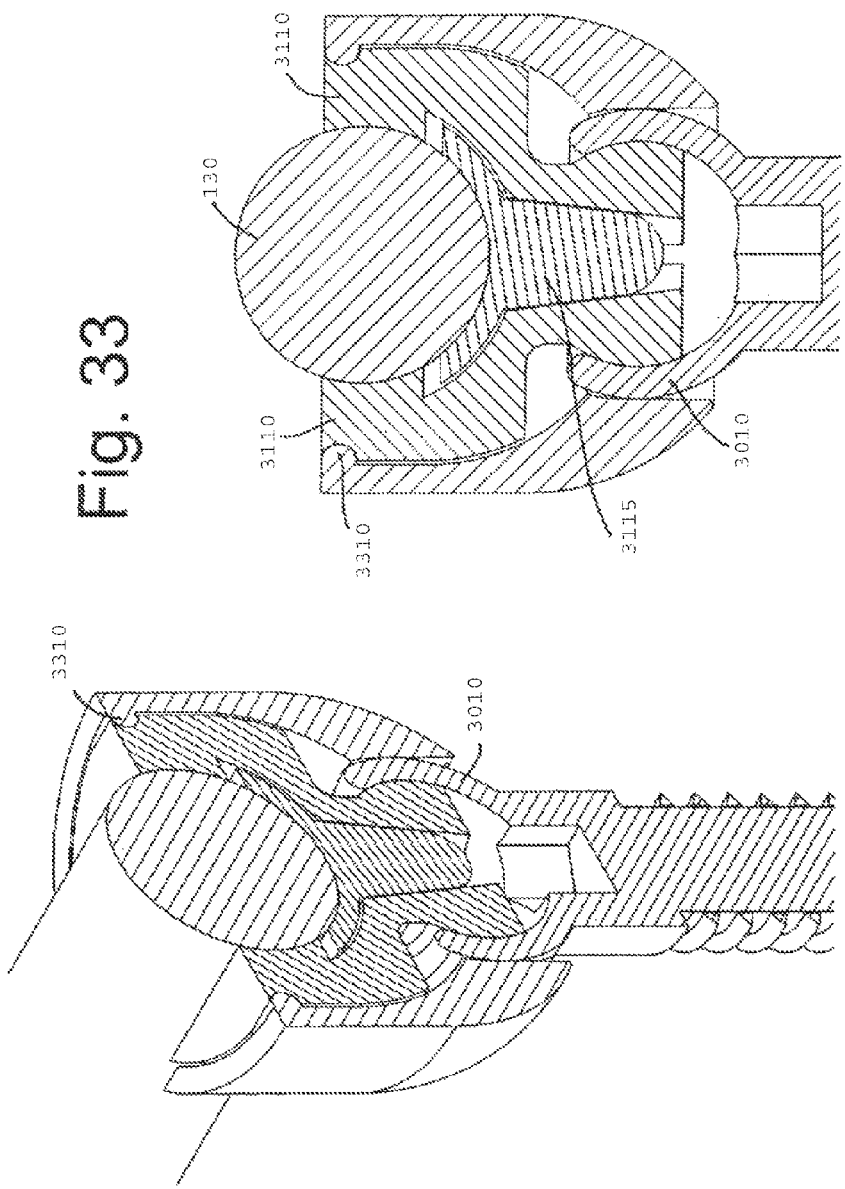
FIG. 33 shows perspective and side cross-sectional views of an upper region of the system.

FIG. 31 shows another embodiment of a bone screw system. FIG. 32 shows the system in an exploded state. FIG. 33 shows perspective and side cross-sectional views of the system. The system includes a bone screw with a head 3010 that is configured in the same manner as the head in the embodiment of FIG. 30. The saddle assembly includes an outer saddle member 3105 that houses a pair of intermediate saddle members 3110. In the assembled device, an inner saddle member 3115 is positioned between the intermediate saddle members such that the inner saddle member and intermediate saddle members collectively form a seat for the rod 130, as shown in FIG. 33.

A pair of protrusions 3310 extend inward from an inner aspect of the outer saddle member 3105. As shown in FIG. 33, the protrusions sit within a slot in the intermediate saddle members 3110. The rod 130 is pushed down to lock the saddle assembly. As the rod 130 is pushed down, it places a downward force onto inner saddle member 3115. The force causes each of the intermediate saddle members 3110 to rotate about the center of the protrusion 3310 so that the lower aspects of the intermediate members 3110 move away from each other.

The lower aspects of the intermediate saddle members 3110 forcefully constrain the bone screw head 3010. As a result, the assembly and rod are immobilized.

Figure 34:
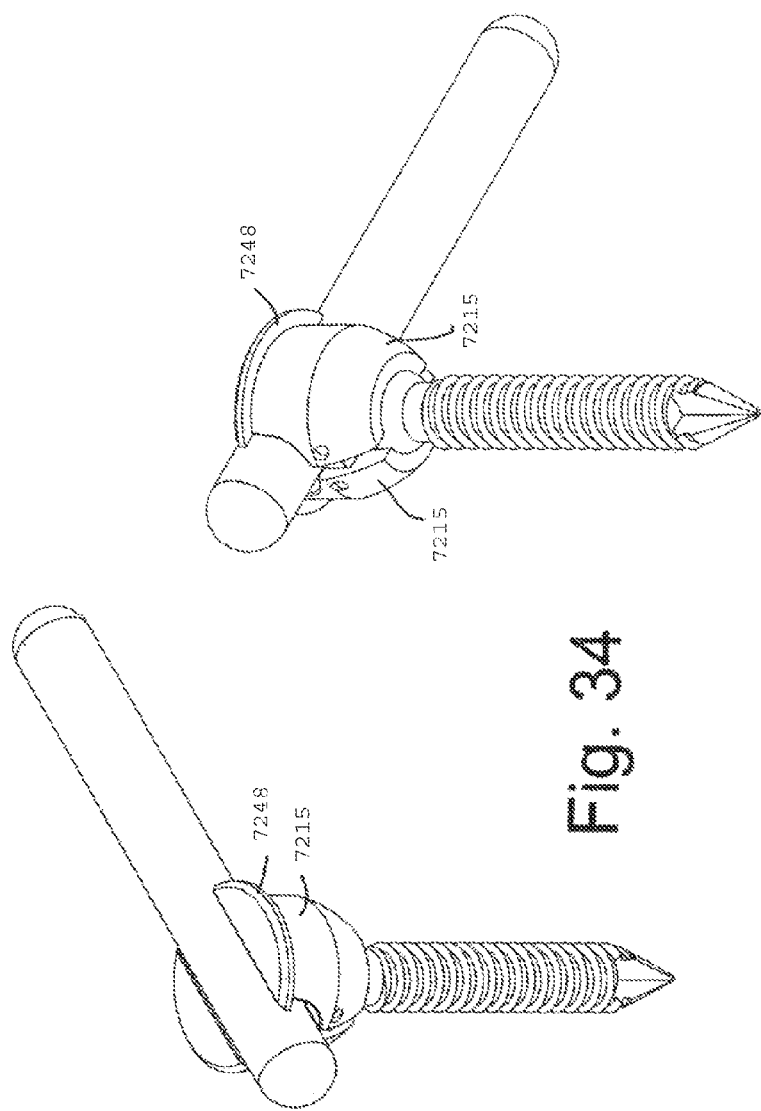
FIG. 34 shows a perspective view of another embodiment of a bone screw system.
Figure 35:
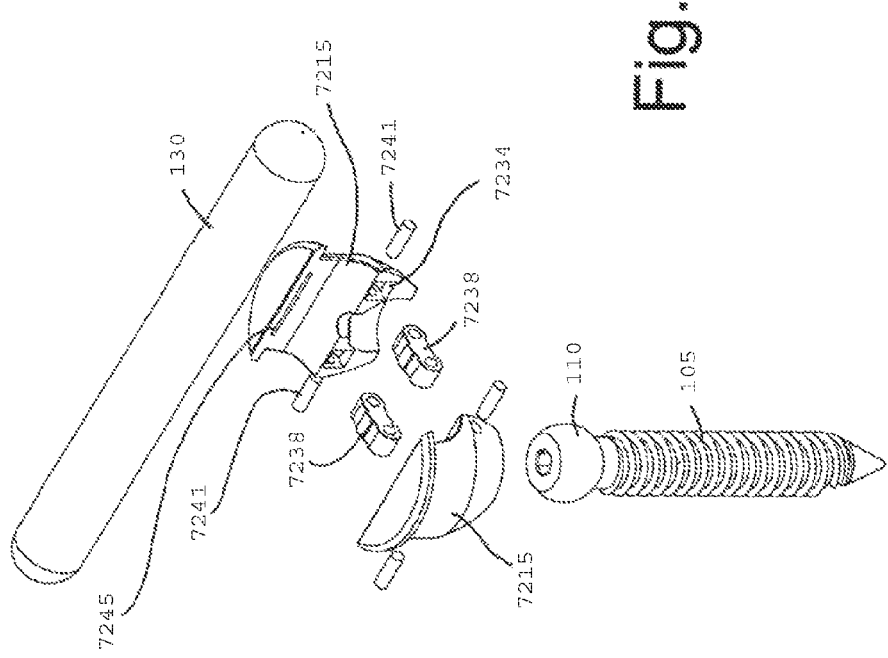
FIG. 35 shows an exploded view of the bone screw system.

FIG. 34 illustrates perspective views of another device embodiment. FIG. 35 shows an exploded view while FIG. 36A illustrates longitudinal sectional views through a hinge member of the device. In FIG. 36B, a horizontal sectional view through the hinge members is shown. With reference to FIG. 35, the device is comprised of two saddle members 7215, bone screw 105 with head 110 and a rod receptacle that is formed by opposing angled walls 7230 (FIG. 36A) of members 7215. Each saddle member 7215 contains at least one side cut-out 7234 that is adapted to at least partially contain a segment of a hinge member 7238.

In assembly, two hinge members 7238 are used to interconnect the two saddle members 7215, wherein, one end of each hinge member 7238 is affixed to a saddle member 7215 by pin 7241 as shown in FIGS. 35 and 36. The device is maintained in the assembled configuration by the action of assembly pins 7241 and given to the surgeon as a unitary device. Note that hinge members 7238 and cut-outs 7234 are collectively configured to insure that the two bottom aspect of each saddle member 7215 can rotate towards but not away from one another. This feature insures that head 110 of screw 105 is securely retained within the assembly even when the device is in the unlocked state. FIG. 36A illustrates longitudinal sectional views through a hinge member of the device. In FIG. 36B, a horizontal sectional view through the hinge members is shown, wherein the line "D" illustrates the section of FIG. 36A.

In application, the bone screw is driven into the underlying bone. A rod 130 is positioned within the rod receptacle formed by opposing angled walls 7230 of members 7215. Because of the angled wall configuration, advancement of rod 130 creates a distractive force between the walls 7230 of the rod-receiving seat of saddle members 7215 and produces rotation of the saddle member relative to the hinge members 7238. With rotation, the inferior segments of the saddle members are driven towards one another and they collectively function as a grasping claw that applies a compressive force onto head 110 of the bone screw. The locking force is provided by a separate implantation instrument (not shown) that pulls upwards onto ledge 7248 as it pushes down onto rod 130. The locking force is maintained even after the instrument is removed by ridged protrusions 7245 or, alternatively, by indentations, ratchets or other retaining features that may be placed on the inner aspects of the rod-receiving seat of the members 7215.

Figure 37:
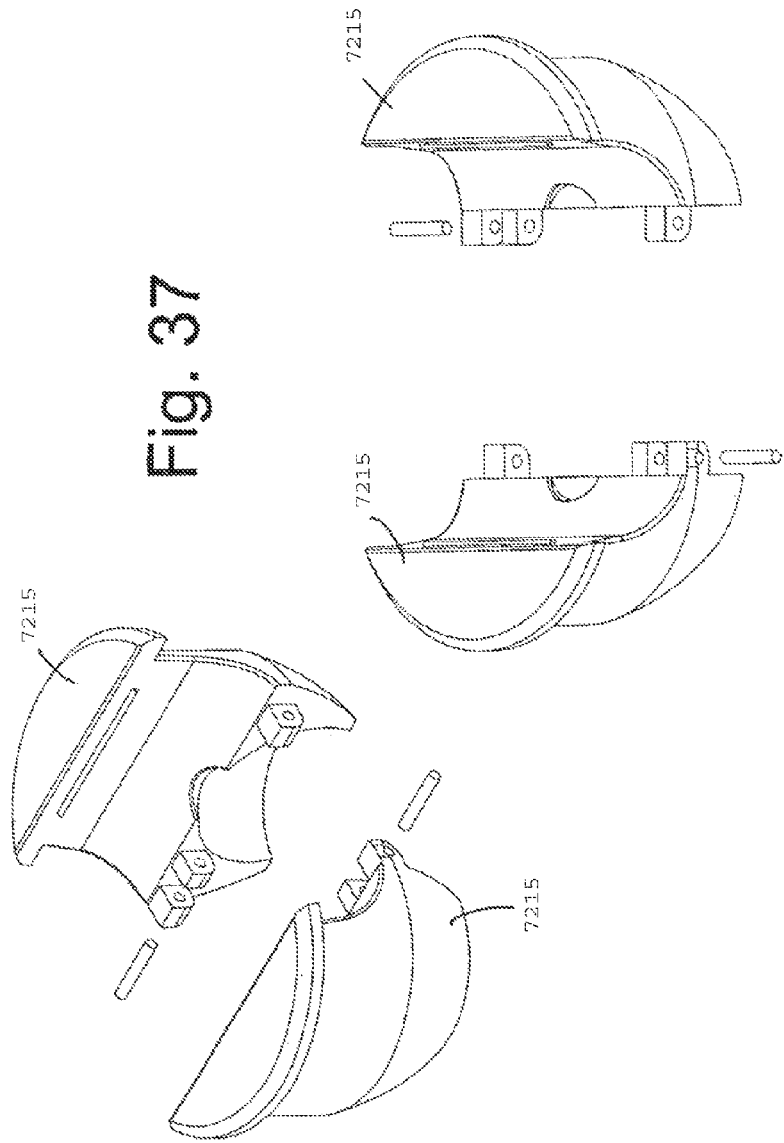
FIG. 37 shows an alternative hinged system embodiment.

The saddle members of an additional hinged device embodiment are shown in FIG. 37. The hinge features are shown as integral members of each member 7215. Unlike the prior embodiment in which there was two rational axis that were off center relative to the long axis of the rod receptacle, the current embodiment has a single central axis of saddle member rotation. The remaining device features are similar to the preceding embodiment.

FIG. 38A shows a perspective view of an additional embodiment. FIG. 38B illustrates an exploded view and FIG. 39 shows cross-sectional views of the embodiment. In this device, a rotational locking member 8233 is positioned between an inner and an outer saddle member. In assembly, the device is maintained in the assembled configuration by the action of assembly pins that movably couple the two saddle members and given to the surgeon as a unitary device. In application, the bone screw is driven into bone. A rod 130 is appropriately positioned within the rod receptacle portion of the saddle members and protrusions 8236 of rotational locking member 8233 are grasped by a locking instrument (not shown). The instrument straddles rod 130 and rotates the protrusions 8236 relative to the stationary rod 130 in order to transition the assembly into the locked configuration. FIGS. 40A and 40B shows a top view of the device in the unlocked and locked configurations, respectively. Note the cooperation between the features of the inner aspect of rotational locking member 8233 and the complimentary features on the outer wall of the inner saddle members. These features produce the inward movement of both inner saddle members and immobilize the device member, bone screw and rod relative to one another. Additional features on the inner aspect of the outer saddle member and the outer aspect of locking member 8233 insure that the locking member rotates smoothly.

FIGS. 41A-41C show top and side views of another embodiment of a bone screw system. FIGS. 42A and 42B show the system in an exploded state. The system includes a bone screw and a saddle assembly that includes an outer saddle member 3705 that removably receives an inner saddle member 3710. As shown in the cross-sectional views of FIGS. 43A and 43B, the inner saddle member 3710 forms a pair of seats that support the head 110 of the bone screw and the rod 130.

FIG. 44A show perspective views of the outer saddle member 3705. The outer saddle member 3705 has a pair of slots 3905 for receipt of the rod 130. An outwardly extending shoulder or lip 3910 is positioned along an upper aspect of the outer saddle member 3705. A small slot 3915 is located in the upper aspect between the slots 3905. The outer saddle member 3705 defines a seat that is sized and shaped to receive the inner saddle member 3710.

FIG. 44B show perspective views of the inner saddle member 3710. A seat 4010 is located on the upper aspect of the inner saddle member 3710 for the rod 130. A slot 4015 extends through the inner saddle member 3710 such that opposed sides of the inner saddle member 3710 are separated by the slot 4015. The slot 4015 permits the opposed sides to flex toward and away from one another. A protrusion 4020 on one side of the inner saddle member 3710 has an opening 4023 that is sized and shaped to receive a pin 4030 (FIG. 42). The opening 4023 is sized such that the pin 4030 can move within the opening 4023 when the pin is positioned therein. A borehole 4025 extends into the inner saddle member 3710 on one side.

Figures 45A, 45B:
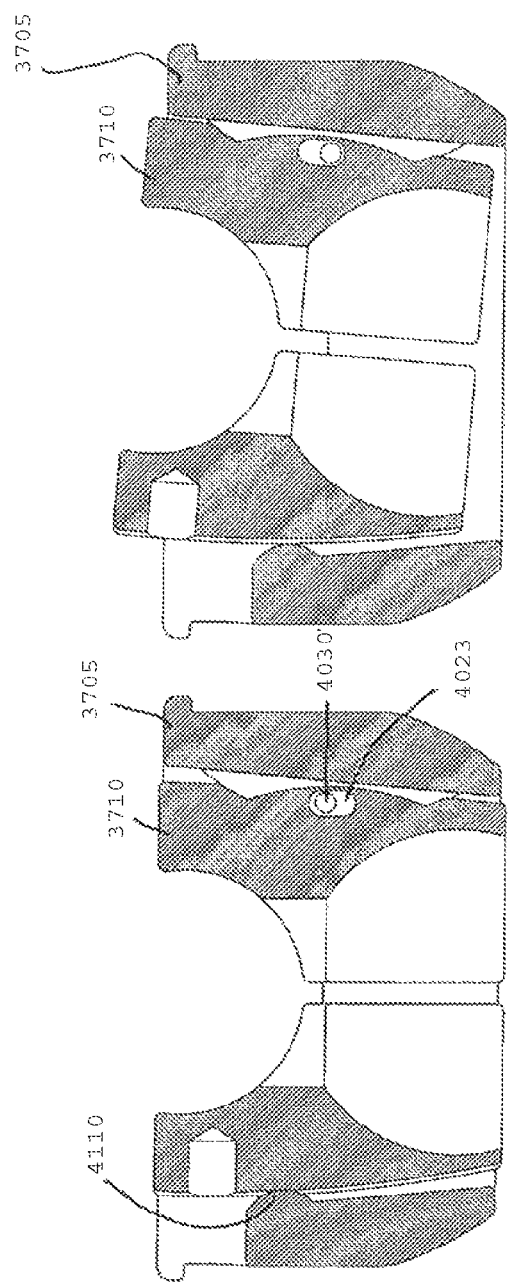
FIGS. 45A and 45B show the assembly in the locked and unlocked configurations, respectively.

FIGS. 45A and 45B show cross-sectional views of the saddle assembly in different states of movement. In FIG. 45A, the inner saddle member 3710 is fully seated in the outer saddle member 3705. The outer saddle member 3705 has an inwardly extending lip 4110 that abuts an outer surface of the inner saddle member 3710. The pin 4030 is positioned in the opening 4023 in the inner saddle member 3710. The pin 4030 also communicates with an opening 3715 (shown in FIG. 42) in the outer saddle member 3705. The pin 4030 links the inner and outer saddle members and serves to limit or govern movement of the inner saddle member within the outer saddle member by virtue of the pin's interaction with the opening 4023. The opening 4023 is larger than the diameter of the pin 4030 to permit the pin to move up and down within the limits of the opening's size.

FIG. 45B shows the saddle assembly with the inner saddle member 3710 moved relative to the outer saddle member 3705. Note that the pin 4030 has moved within the opening 4023 relative to the position shown in FIG. 45A. Moreover, a side region of the inner saddle member 3710 has moved upward relative to the outer saddle member 3705. The lip 4110 provides a bearing surface against the outer surface of the inner saddle member 3710 to guide movement between the inner and outer saddle members. In the assembled device, the head of the bone screw is positioned within the space 4120 such that the bone screw head can move along with the inner saddle relative to the outer saddle.

Figure 47:
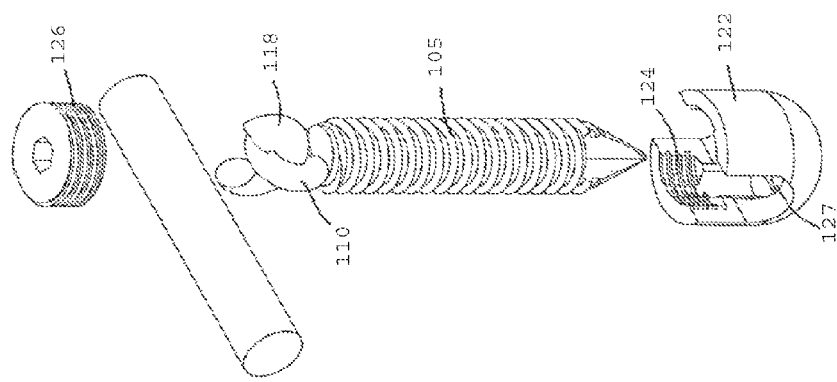
FIG. 47 shows an exploded view of the device in FIG. 46.

While all of the previous embodiments provide relative movement between the screw system assembly and the bone screw in the unlocked state, some surgical applications may require a greater angle of allowable movement during screw system implantation. FIG. 46A shows a perspective view of an assembled screw system embodiment that permits greater movement between the locking assembly and the bone screw. FIG. 46B shows side views of the device. FIG. 47 illustrates an exploded view while FIGS. 48A and 48B show cross-sectional views. The bone screw has a threaded shank 105 and a toroid head 110 with central aperture 112. A second, complimentary toroid member 118 is positioned within aperture 112 and forms an articulation with the bone screw. Toroid member 118 can move freely relative to the bone screw in each of two substantially perpendicular planes but can not rotate independent of the bone screw. An outer housing 122 houses the bone screw and member 118. The proximal end of housing 122 has threads 124 that are adapted to engage the threads of a complimentary locking nut 126. The distal end of housing 122 has an aperture 127 that is of lesser diameter that the diameter of toroid member 118. In assembly, member 118 is positioned within the central aperture 112 of the bone screw and both members are retained within housing 122 by distal aperture 127. This screw system design allows more than one hundred degrees of movement between the bone screw and the housing member 122 in each of the two perpendicular planes of allowable movement.

In application, the bone screw is anchored into an underlying bone. The bone screw is rotated and driven into bone by a screw driver (not shown) that is adapted to engage and rotate "eye screw" bolts. These screw drivers are well known in the art and are commonly available. Housing 122 is appropriately positioned relative to the bone screw and rod 130 is placed within the rod-receiving seat of housing 122. Locking nut 126 engages threads 124. With rotation and advancement, nut 126 will propel rod 130 into contact with a segment of toroid head 110 of the bone screw. With continued nut advancement, rod 130 will exert a downward force onto the bone screw and an upward force upon housing 122. In this way, the bone screw, toroid member 118, rod 130 and housing member 122 will be collectively immobilized relative to one another. In FIG. 48A, the locked assembly is shown in sectional views that are perpendicular to the log axis of rod 130 while FIG. 48B illustrates sectional views in the direction of the rod.

Devices embodiments without a locking nut can be also designed to permit a greater angle of movement between the locking assembly and the bone screw prior to assembly immobilization. With reference to the embodiment of FIGS. 41 to 45, for example, the inner saddle member may be modified to provide a larger angle of movement between the bone screw and the assembly in a desired direction. FIG. 49 illustrates an inner saddle member that has a sloped bottom surface 4215 and allows greater movement relative to the bone screw, as described below. The inner saddle member 4210 is sized and shaped relative to the outer saddle member 3705 to provide greater relative movement therebetween in a desired direction than the previous embodiment of the inner saddle member 3710. FIG. 50 shows side views of the inner saddle member with cross-sectional features shown in phantom lines.

Figure 52B:
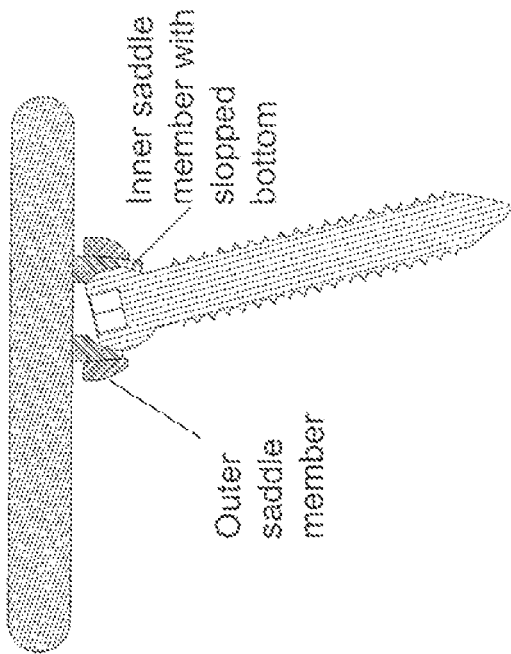
FIGS. 52A and 52B show an alternative embodiment adapted to allow a range of movement for the bone screw which is biased towards a preferred direction.
Figure 52A:
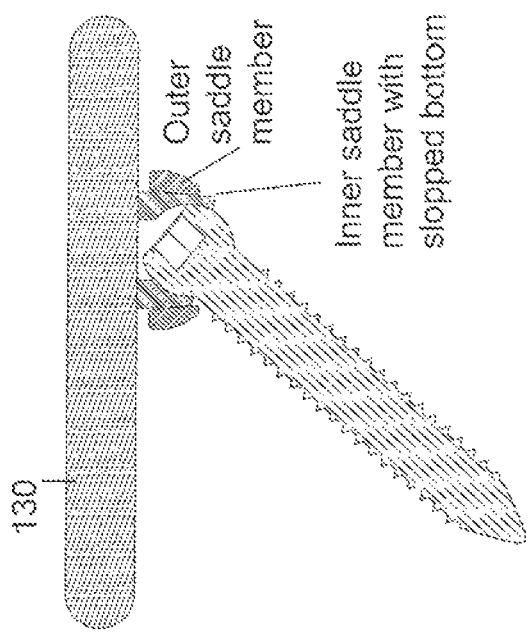

These modifications of the inner saddle member can be similarly employed in other device embodiments. A representative embodiment of those devices without a locking nut, for example, is shown in FIG. 51. The assembled device is illustrated in FIG. 51A, the exploded device is shown in FIG. 51B and a sectional view is shown in FIG. 51C. Cross-sectional views of the modified device containing an inner saddle member with a slopped bottom surface is shown in FIG. 52 and the screw's range of movement is illustrated. The head of the bone screw can rotate within the seat formed by the inner saddle member. The sloped bottom surface of the modified inner saddle member permits the bone screw to rotate to a greater left-most position than if the bottom surface were not sloped. FIG. 53 shows a cross-sectional view of another embodiment of the assembled system in which the upper surfaces of both the inner and outer saddle members are sloped in order to permit a sloped orientation of the rod 130.

The disclosed devices or any of their components can be made of any biologically adaptable or compatible materials. Materials considered acceptable for biological implantation are well known and include, but are not limited to, stainless steel, titanium, tantalum, combination metallic alloys, various plastics, resins, ceramics, biologically absorbable materials and the like. Any components may be also coated/made with osteo-conductive (such as deminerized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, any surface may be at least partially made with bone, bone substitute and/or a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. Lastly, the system or any of its components can also be entirely or partially made of a shape memory material or other deformable material.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A bone fastener assembly, comprising:
an elongated interconnecting member;
a bone fixation member comprising a first segment configured to be attached onto a skeletal bone and a second segment at least partially seated within an inner housing member;
the inner housing member comprising a first seat configured to receive a segment of the elongated interconnecting member and a second seat configured to receive the second segment of the bone fixation member, the inner housing member being comprised of at least two movable members each forming at least a segment of the first seat and the second seat; and
an outer housing member comprising a seat configured to receive at least a portion of the inner housing and a locking feature that is configured to transition the assembly from a first state to a second state;
wherein in the first state, the bone fixation member is mobile relative to the elongated interconnecting member, and in the second state, the bone fixation member is immobilized relative to the elongated interconnecting member;

wherein the locking feature is separated from direct abutment with the inner housing member; and wherein transition of the locking feature from the first to the second state produces an increase in a diameter of the first seat of the inner housing member and a reduction in a diameter of the second seat with immobilization of the bone fixation member therein.

2. A bone fastener assembly as in claim 1, wherein the interconnecting member is a rod.

3. A bone fastener assembly as in claim 1, wherein the bone fixation member is a screw.

4. A bone fastener assembly as in claim 3, wherein the first segment comprises external threads.

5. A bone fastener assembly as in claim 3, wherein the second segment is of larger diameter than the first segment.

6. A bone fastener assembly as in claim 1, wherein the bone fixation member is a multi-segmental screw assembly.

7. A bone fastener assembly as in claim 6, wherein the bone fixation member comprises:
   an assembly comprising an outer wall that is at least partially threaded, the assembly configured to extend distally along a central axis from a proximal aspect, and comprising at least a proximal segment and a distal threaded segment; and
   the proximal segment extending from a proximal aspect to a distal end and the distal threaded segment extending from a proximal aspect to a distal end;
   wherein the proximal and distal threaded segments are sequentially aligned along the central axis, and the distal end of the proximal segment abuts a proximal segment of the distal threaded segment; and
   wherein the proximal segment further comprises at least one expansion aperture within a portion of an outer wall, the expansion aperture configured to permit radial outward expansion of at least a portion of the outer wall of the proximal segment.

8. A bone fastener assembly as in claim 1, wherein the locking feature is an assembly comprising:
   a threaded screw; and
   a housing member comprising a central threaded aperture, at least one radial aperture and an external surface;
   wherein the threaded central aperture is configured to threadedly engage the threaded screw;
   wherein the at least one radial aperture comprises a movable member configured to extend from a retracted position to an extended position within the radial aperture; and
   wherein, in the extended position, at least a segment of the movable member extends beyond the external surface of the housing member.

9. A bone fastener assembly as in claim 8, wherein the movable member is biased towards the extended position.

10. A bone fastener assembly as in claim 8, wherein the movable member is retained within an aperture of the outer housing member.

11. A bone fastener assembly as in claim 1, wherein at least a component of the assembly is manufactured from a metallic alloy.

12. A bone fastener assembly as in claim 11, wherein the metallic alloy is at least partially comprised of Titanium.

13. A bone fastener assembly as in claim 1, wherein at least a component of the assembly is configured to contain a bioactive material configured to promote the bone ingrowth into a segment of the assembly.

14. A bone fastener assembly as in claim 1, wherein at least a component of the assembly is configured to contain a bioactive material configured to establish a mineralized connection between an adjacent bone and a segment of the assembly.

15. A bone fastener assembly, comprising:
   an elongated interconnecting member;
   a bone fixation member comprising a first segment configured to be attached onto a skeletal bone and a second segment at least partially seated within an inner housing member;
   the inner housing member comprising a first seat configured to receive a segment of the elongated interconnecting member and a second seat configured to receive the second segment of the bone fixation member, the inner housing being comprised of at least two movable members each forming at least a segment of the first seat and the second seat; and
   an outer housing member comprising a seat configured to receive at least a portion of the inner housing, and a locking feature configured to transition the assembly from a first state to a second state;
   wherein, in the first state, the bone fixation member is mobile relative to the outer housing member, and in the second state, the bone fixation member is immobilized relative to the outer housing member; and
   wherein the locking feature is configured to abut and advance the interconnecting member into the first seat of the inner housing member, thereby increasing a diameter of the first seat while concurrently reducing a diameter of the second seat of the inner housing, and wherein removal of the elongated interconnecting member prevents immobilization of the bone fixation member relative to the outer housing member.

16. A bone fastener assembly as in claim 15, wherein the interconnecting member is a rod.

17. A bone fastener assembly as in claim 15, wherein the bone fixation member is a screw.

18. A bone fastener assembly as in claim 17, wherein the first segment comprises external threads.

19. A bone fastener assembly as in claim 17, wherein the second segment is of larger diameter than the first segment.

20. A bone fastener assembly as in claim 15, wherein the bone fixation member is a multi-segmental screw assembly.

21. A bone fastener assembly as in claim 20, wherein the bone fixation member comprises:
   an assembly comprising an outer wall that is at least partially threaded, the assembly configured to extend distally along a central axis from a proximal aspect, and comprising at least a proximal segment and a distal threaded segment;
   wherein the proximal segment extends from a proximal aspect to a distal end and the distal threaded segment extends from a proximal aspect to a distal end;
   wherein the proximal and distal threaded segments are sequentially aligned along the central axis, and the distal end of the proximal segment abuts a proximal segment of the distal threaded segment;
   wherein the proximal segment further comprises at least one expansion aperture within a portion of an outer wall, the expansion aperture configured to permit radial outward expansion of at least a portion of the outer wall of the proximal segment.

22. A bone fastener assembly as in claim 15, wherein the locking feature is an assembly comprising:
   a threaded screw;
   a housing member comprising a central threaded aperture, at least one radial aperture and an external surface, the threaded central aperture configured to threadedly engage the threaded screw;

wherein the at least one radial aperture comprises a movable member configured to extend from a retracted position to an extended position within the radial aperture; and wherein, in the extended position, at least a segment of the movable member extends beyond the external surface of the housing member.

23. A bone fastener assembly as in claim 22, wherein the movable member is biased towards the extended position.

24. A bone fastener assembly as in claim 22, wherein the movable member is retained within an aperture of the outer housing member.

25. A bone fastener assembly as in claim 15, wherein at least a component of the assembly is manufactured from a metallic alloy.

26. A bone fastener assembly as in claim 25, wherein the metallic alloy is at least partially comprised of Titanium.

27. A bone fastener assembly as in claim 15, wherein at least a component of the assembly is configured to contain a bio-active material configured to promote the bone ingrowth into a segment of the assembly.

28. A bone fastener assembly as in claim 15, wherein at least a component of the assembly is configured to contain a bio-active material configured to establish a mineralized connection between an adjacent bone and a segment of the assembly.

29. A bone fastener assembly comprising:
a bone fixation member;
an elongated interconnecting member; and
a first housing member comprising at least a first seat, a second seat, and a locking assembly, the first seat comprises at least a first segment of the interconnecting member, the second seat comprises at least a first segment of the bone fixation member,
the locking assembly comprising:
    a fastener;
    a second housing comprising an external surface, a first internal bore configured to accept the fastener, and at least one aperture configured to extend from the first internal bore to the external surface; and
    a movable member at least partially contained within the aperture, the movable member configured to extend from a retracted position to an extended position, in the extended position, at least a segment of the movable member extends beyond the external surface of the second housing member;
wherein the movable member is biased towards the extended position;
wherein the fastener is further configured to extend from a proximal end to a distal end and a distal segment of the fastener being configured to advance through the internal bore, the distal end of the locking assembly being configured to be positioned above the at least one aperture thereby enabling the locking assembly to be advanced into an internal bore of the first housing member;
wherein, when the distal end of the fastener is below the at least one aperture, the locking assembly is prevented from advancement into the housing member.

30. A bone fastener assembly as in claim 29, wherein the bone fastener is a bone screw.

31. A bone fastener assembly as in claim 29, wherein the elongated interconnecting member is a rod.

32. A bone fastener assembly as in claim 29, wherein the fastener of the locking assembly is a threaded screw.

33. A bone fastener assembly as in claim 29, wherein the movable member is biased towards the extended position by a resilient member.

34. A bone fastener assembly as in claim 29, wherein at least a segment of the movable member extends into a cavity of the first housing member and retains the locking assembly attached to the first housing member.

35. A bone fastener assembly as in claim 29, wherein advancement of the fastener into the first internal bore of the second housing transitions the bone fastener assembly from a first state to a second state;
wherein, in the first state, the bone fixation member is mobile relative to the elongated interconnecting member; and
wherein, in the second state, the first segment of the bone fixation member is immobilized relative to the first segment of the elongated interconnecting member.

36. A bone fastener assembly comprising:
a bone fixation member;
an elongated interconnecting member;
a first housing member comprising a first seat configured to receive at least a segment of the elongated interconnecting member, a second seat configured to receive at least a segment of the bone fixation member, and a locking mechanism assembly sized to be advanced onto the interconnecting member through an internal bore of the first housing member;
wherein the locking mechanism assembly comprises:
    a second housing member comprising an upper surface, an opposing lower surface and a side surface configured to connect the upper and lower surfaces, a second internal bore of the locking mechanism being configured to connect the upper and lower surfaces, and at least one aperture being formed from an opening on a wall of the second internal bore to an opening on the side surface;
    a movable member comprising at least a segment configured to advance through the at least one aperture and to extend from a retracted position to an extended position, wherein in the extended position, said segment of the movable member extends beyond an external perimeter of the second housing member and prevents advancement of the locking mechanism into the first housing; and
    a locking member configured to extend from a proximal end to a distal end and comprising a distal segment configured to advance through the second internal bore, the distal end of the locking member is configured to be positioned above the at least one aperture of the second internal bore, thereby enabling the locking mechanism assembly to be advanced into the internal bore of the first housing member;
wherein, when the distal end of the locking mechanism is below the aperture, the locking member assembly is prevented from advancement into the first housing member.

* * * * *